US012753219B2

(12) United States Patent
Budde et al.

(10) Patent No.: US 12,753,219 B2
(45) Date of Patent: Oct. 6, 2026

(54) CCR4 TARGETED CHIMERIC ANTIGEN RECEPTOR MODIFIED T CELLS FOR TREATMENT OF CCR4 POSITIVE MALIGNANCIES

(71) Applicant: City of Hope, Duarte, CA (US)

(72) Inventors: Lihua Elizabeth Budde, Duarte, CA (US); Marissa M. Del Real, Duarte, CA (US); Stephen Forman, Duarte, CA (US)

(73) Assignee: City of Hope, Duarte, CA (US)

( * ) Notice: Subject to any disclaimer, the term of this patent is extended or adjusted under 35 U.S.C. 154(b) by 1212 days.

(21) Appl. No.: 17/612,794

(22) PCT Filed: May 22, 2020

(86) PCT No.: PCT/US2020/034389
§ 371 (c)(1),
(2) Date: Nov. 19, 2021

(87) PCT Pub. No.: WO2020/243007
PCT Pub. Date: Dec. 3, 2020

(65) Prior Publication Data

US 2022/0249560 A1 Aug. 11, 2022

Related U.S. Application Data

(60) Provisional application No. 62/852,934, filed on May 24, 2019.

(51) Int. Cl.

| | |
|---|---|
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C07K 14/725*** | (2006.01) |
| ***C07K 16/28*** | (2006.01) |
| ***C12N 5/0783*** | (2010.01) |
| *A61K 39/00* | (2006.01) |

(52) U.S. Cl.
CPC .......... *C07K 14/7051* (2013.01); *A61K 40/11* (2025.01); *A61K 40/31* (2025.01); *A61K 40/4219* (2025.01); *A61P 35/00* (2018.01); *C07K 16/2866* (2013.01); *C12N 5/0636* (2013.01); *C12N 5/0638* (2013.01); *A61K 2039/505* (2013.01); *A61K 2239/31* (2023.05); *A61K 2239/38* (2023.05); *A61K 2239/48* (2023.05)

(58) Field of Classification Search
CPC ............ C07K 14/7051; C07K 16/2866; C07K 14/70503; C07K 14/7158; C07K 2317/24; C07K 2317/622; C07K 2317/73; C07K 2319/03; A61K 40/11; A61K 40/31; A61K 40/4219; A61K 2039/505; A61K 2239/31; A61K 2239/38; A61K 2239/48; A61P 35/00; C12N 5/0636; C12N 5/0638; C12N 2510/00; C12N 15/86
See application file for complete search history.

(56) References Cited

U.S. PATENT DOCUMENTS

| | | | | |
|---|---|---|---|---|
| 8,962,806 B2 * | 2/2015 | Marasco | ............ | C07K 16/2866 530/391.1 |
| 9,499,629 B2 * | 11/2016 | June | ........................ | A61P 43/00 |
| 9,914,909 B2 * | 3/2018 | Brown | ................... | A61K 40/31 |
| 10,221,245 B2 * | 3/2019 | Brogdon | .......... | C07K 14/70503 |

FOREIGN PATENT DOCUMENTS

| | | |
|---|---|---|
| CN | 103328513 | 9/2013 |
| CN | 107429253 | 12/2017 |
| JP | 2017-537627 | 12/2017 |
| JP | 2017-537972 A | 12/2017 |
| JP | 2018-531015 | 10/2018 |
| JP | 2019-536469 | 12/2019 |
| JP | 2020-511498 | 4/2020 |
| WO | WO 2016/057488 A1 | 4/2016 |
| WO | WO 2016090369 | 6/2016 |
| WO | WO 2017015490 | 1/2017 |
| WO | WO 2017/066481 | 4/2017 |
| WO | WO 2018057585 | 3/2018 |
| WO | WO 2018102761 | 6/2018 |
| WO | WO 2018/175453 | 9/2018 |
| WO | WO 2020243007 | 12/2020 |

OTHER PUBLICATIONS

Chang et al., "Humanization of an anti-CCR4 antibody that kills Cutaneous T-Cell Lymphoma cells and abrogates suppression by T-regulatory cells," Mol. Cancer Ther, Nov. 2012, 11:2451-61.

(Continued)

*Primary Examiner* — Christopher M Babic
*Assistant Examiner* — Masudur Rahman

(57) ABSTRACT

Chimeric antigen receptors (CAR) for use in treating lymphoma-associated C-C chemokine receptor type 4 (CCR4) and other cancers expressing CCR4 comprise a CCR4 targeting domain (i.e., a CCR4 targeted single chain variable fragment or variant thereof). A population of autologous or allogeneic T cells expressing a CCR4-targeted CAR (e.g., transduced by a nucleic acid molecule encoding the CAR can be administered as a method of treating CCR4 positive cancers (including, e.g., peripheral T cell lymphoma, adult T cell lymphoma, anaplastic large cell lymphoma, primary cutaneous T cell lymphoma, renal cell carcinoma, lung cancer, hepatocellular carcinoma, and diffuse large B-cell lymphoma).

12 Claims, 30 Drawing Sheets

Specification includes a Sequence Listing.

(56) References Cited

OTHER PUBLICATIONS

Das et al., "Tet-On Systems for Doxycycline-inducible Gene Expression," Current Gene Therapy, 2016, 16(3):156-167.
International Preliminary Report on Patentability in International Application No. PCT/US2020/034389, dated Dec. 2, 2021, 10 pages.
International Search Report and Written Opinion in International Application No. PCT/US2020/034389, dated Nov. 13, 2020, 19 pages.
Invitation to Pay Additional Fees and, Where Applicable, Protest Fee in International Application No. PCT/US2020/034389, dated Sep. 22, 2020, 14 pages.
Perera et al., "Chimeric antigen receptor modified T cells that target chemokine receptor CCR4 as a therapeutic modality for T-cell malignancies," American Journal of Hematology, Jun. 5, 2017, 92(9):892-901.
Priceman et al., "Co-stimulatory signaling determines tumor antigen sensitivity and persistence of CAR T cells targeting PSCA+ metastatic prostate cancer," Oncoimmunology, Oct. 16, 2017, 7(2):e1380764.
Tang et al., "Optimization of lentiviral vector production using polyethylenimine-mediated transfection," Oncology letters, Jan. 2015, 9(1):55-62.
Wang et al., "Engraftment of human central memory-derived effector CD8+ T cells in immunodeficient mice," Blood, Feb. 10, 2011, 117(6):1888-1898.
Wang et al., "Lenalidomide Enhances the Function of CS1 Chimeric Antigen Receptor-Redirected T Cells Against Multiple Myeloma, " Clinical Cancer Research, Jan. 2018, 24(1):106-119.
Yonekura et al., "Effect of anti-CCR4 monoclonal antibody (mogamulizumab) on adult T-cell leukemia-lymphoma: Cutaneous adverse reactions may predict the prognosis," J Dermatol, Mar. 17, 2014, 41(3):239-244.
Mamonkin et al., "Reversible Transgene Expression Reduces Fratricide and Permits 4-1BB Costimulation of CAR T Cells Directed to T-cell Malignancies," Cancer Immunology Research, Jan. 2018, 6(1):47-58.

* cited by examiner

CCR4 CAR 1: CCR4scFv-L-CD4tm-41BB-CD3ζ-T2A-EGFRt

CCR4 CAR 2: CCR4scFv-IgG4(L235E, N297Q)-CD4tm-41BB-CD3 ζ-T2A-EGFRt

CCR4 CAR 3: CCR4scFv-IgG4(HL-CH3)-CD4tm-41BB-Zeta(CO)-T2A-EGFRt

FIG. 1

1. huCCR4scFv-L-CD4tm-41BB-Zeta(CO)-T2A-EGFRt_epHIV7
2. huCCR4scFv-IgG4(L235E, N297Q)-CD4tm-41BB-Zeta(CO)-T2A-EGFRt_epHIV7
3. huCCR4scFv-IgG4(HL-CH3)-CD4tm-41BB-Zeta(CO)-T2A-EGFRt_epHIV7

CCR4scFv-Linker-CD4tm-41BB-Zeta

MLLLVTSLLLCELPHPAFLLIPQVQLVQSGAEVKKPGASVKVSCKASGYTFASYYMHWMRQ

GMCSFRa signal peptide CCR4scFv

APGQGLEWIGWINPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGERATINCKSSQS

ILYSSNQKNYLAWYQQKPGQSPKLLIYWASTRESGVPDRFSGSGSGTDFTLTISSLQAEDVAV

YYCHQYLSSYTFGQGTKLEIKGGGSSGGGSGMALIVLGGVAGLLLFIGLGIFFKRGRKKLLYIFK

Linker CD4 transmembrane 4-1BB

QPFMRPVQTTQEEDGCSCRFPEEEEGGCELGGGRVKFSRSADAPAYQQGQNQLYNELNLG (Gly)3 Zeta

RREEYDVLDKRRGRDPEMGGKPRRKNPQEGLYNELQKDKMAEAYSEIGMKGERRRGKGH

DGLYQGLSTATKDTYDALHMQALPPR

FIG. 10A

CCR4scFv-IgG4(L235E,N297Q)-CD4tm-41BB-Zeta

MLLLVTSLLLCELPHPAFLLIPQVQLVQSGAEVKKPGASVKVSCKASGYTFASYYMHWMRQ

GMCSFRa signal peptide CCR4scFv

APGQGLEWIGWINPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGERATINCKSSQS

ILYSSNQKNYLAWYQQKPGQSPKLLIYWASTRESGVPDRFSGSGSGTDFTLTISSLQAEDVAV

YYCHQYLSSYTFGQGTKLEIKESKYGPPCPPCPAPEFEGGPSVFLFPPKPKDTLMISRTPEVTC

IgG4(SmP)

VVVDVSQEDPEVQFNWYVDGVEVHNAKTKPREEQFQSTYRVVSVLTVLHQDWLNGKEYK

CKVSNKGLPSSIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHNHYTQKSLSLS

LGKMALIVLGGVAGLLLFIGLGIFFKRGRKKLLYIFKQPFMRPVQTTQEEDGCSCRFPEEEEGG

CD4 transmembrane 4-1BB

CELGGGRVKFSRSADAPAYQQGQNQLYNELNLGRREEYDVLDKRRGRDPEMGGKPRRKN (Gly)3 Zeta

PQEGLYNELQKDKMAEAYSEIGMKGERRRGKGHDGLYQGLSTATKDTYDALHMQALPPR

FIG. 10B

CR4scFv-IgG4(HL-CH3)-CD4tm-41BB-Zeta

MLLLVTSLLLCELPHPAFLLIPQVQLVQSGAEVKKPGASVKVSCKASGYTFASYYMHWMRQ

GMCSFRa signal peptide CCR4scFv

APGQGLEWIGWINPGNVNTKYNEKFKGRATLTVDTSTNTAYMELSSLRSEDTAVYYCARST
YYRPLDYWGQGTLVTVSSSGGGSGGGGSGGGGSDIVMTQSPDSLAVSLGERATINCKSSQS
ILYSSNQKNYLAWYQQKPGQSPKLLIYWASTRESGVPDRFSGSGSGTDFTLTISSLQAEDVAV
YYCHQYLSSYTFGQGTKLEIKESKYGPPCPPCPGGGSSGGGSGGQPREPQVYTLPPSQEEMT

IgG4(SmP)-Hinge Linker IgG4-CH3

KNQVSLTCLVKGFYPSDIAVEWESNGQPENNYKTTPPVLDSDGSFFLYSRLTVDKSRWQEG
NVFSCSVMHEALHNHYTQKSLSLSLGKMALIVLGGVAGLLLFIGLGIFFKRGRKKLLYIFKQPF

CD4 transmembrane 4-1BB

MRPVQTTQEEDGCSCRFPEEEEGGCELGGGRVKFSRSADAPAYQQGQNQLYNELNLGRRE (Gly)3 Zeta

EYDVLDKRRGRDPEMGGKPRRKNPQEGLYNELQKDKMAEAYSEIGMKGERRRGKGHDGL
YQGLSTATKDTYDALHMQALPPR

FIG. 10C inducibleCCR4 CAR 1: CCR4scFv-IgG4(L235E, N297Q)-CD4tm-41BB-CD3 ζ-T2A-CD19t
inducibleCCR4 CAR 2: CCR4scFv-IgG4(HL-CH3)-CD4tm-41BB-Zeta(CO)-T2A-CD19t
inducibleCCR4 CAR 3: CCR4scFv-IgG4(L235E, N297Q)-CD4tm-41BB-CD3 ζ
inducibleCCR4 CAR 4: CCR4scFv-IgG4(HL-CH3)-CD4tm-41BB-Zeta(CO)

FIG. 13A

TREp-huCCR4scFv-IgG4(L235E,N297Q)-CD4tm-41BB-Zeta_EF1p-tTA-T2A-CD19t_epHIV7

TREp-huCCR4scFv-IgG4(HL-CH3)-CD4tm-41BB-Zeta_EF1p-tTA-T2A-CD19t_epHIV7

TREp-huCCR4scFv-IgG4(L235E,N297Q)-CD4tm-41BB-Zeta_EF1p-tTA_epHIV7

TREp-huCCR4scFv-IgG4(HL-CH3)-CD4tm-41BB-Zeta_EF1p-tTA_epHIV7

CCR4scFv-Linker-CD4tm-41BB-Zeta

QVQLVQSGAEVKKPGASVKVSCKASGYTFASYYMHWMRQ

CCR4scFv

APGQGLEWIGWINPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGERATINCKSSQS

ILYSSNQKNYLAWYQQKPGQSPKLLIYWASTRESGVPDRFSGSGSGTDFTLTISSLQAEDVAV

YYCHQYLSSYTFGQGTKLEIKGGGSSGGGSGMALIVLGGVAGLLLFIGLGIFFKRGRKKLLYIFK

Linker CD4 transmembrane 4-1BB

QPFMRPVQTTQEEDGCSCRFPEEEEGGCELGGGRVKFSRSADAPAYQQGQNQLYNELNLG (Gly)3 Zeta

RREEYDVLDKRRGRDPEMGGKPRRKNPQEGLYNELQKDKMAEAYSEIGMKGERRRGKGH

DGLYQGLSTATKDTYDALHMQALPPR

FIG. 14A

CCR4scFv-IgG4(L235E,N297Q)-CD4tm-41BB-Zeta

QVQLVQSGAEVKKPGASVKVSCKASGYTFASYYMHWMRQ

CCR4scFv

APGQGLEWIGWINPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGERATINCKSSQS

ILYSSNQKNYLAWYQQKPGQSPKLLIYWASTRESGVPDRFSGSGSGTDFTLTISSLQAEDVAV

YYCHQYLSSYTFGQGTKLEIKESKYGPPCPPCPAPEFEGGPSVFLFPPKPKDTLMISRTPEVTC

IgG4(SmP)

VVVDVSQEDPEVQFNWYVDGVEVHNAKTKPREEQFQSTYRVVSVLTVLHQDWLNGKEYK

CKVSNKGLPSSIEKTISKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHEALHNHYTQKSLSLS

LGKMALIVLGGVAGLLLFIGLGIFFKRGRKKLLYIFKQPFMRPVQTTQEEDGCSCRFPEEEEGG

CD4 transmembrane 4-1BB

CELGGGRVKFSRSADAPAYQQGQNQLYNELNLGRREEYDVLDKRRGRDPEMGGKPRRKN (Gly)3 Zeta

PQEGLYNELQKDKMAEAYSEIGMKGERRRGKGHDGLYQGLSTATKDTYDALHMQALPPR

FIG. 14B

CR4scFv-IgG4(HL-CH3)-CD4tm-41BB-Zeta

QVQLVQSGAEVKKPGASVKVSCKASGYTFASYYMHWMRQ

CCR4scFv

APGQGLEWIGWINPGNVNTKYNEKFKGRATLTVDTSTNTAYMELSSLRSEDTAVYYCARST
YYRPLDYWGQGTLVTVSSSGGGSGGGGSGGGGSDIVMTQSPDSLAVSLGERATINCKSSQS
ILYSSNQKNYLAWYQQKPGQSPKLLIYWASTRESGVPDRFSGSGSGTDFTLTISSLQAEDVAV
YYCHQYLSSYTFGQGTKLEIKESKYGPPCPPCPGGGSSGGGSGGQPREPQVYTLPPSQEEMT

IgG4(SmP)-Hinge Linker IgG4-CH3

KNQVSLTCLVKGFYPSDIAVEWESNGQPENNYKTTPPVLDSDGSFFLYSRLTVDKSRWQEG
NVFSCSVMHEALHNHYTQKSLSLSLGKMALIVLGGVAGLLLFIGLGIFFKRGRKKLLYIFKQPF

CD4 transmembrane 4-1BB

MRPVQTTQEEDGCSCRFPEEEEGGCELGGGRVKFSRSADAPAYQQGQNQLYNELNLGRRE (Gly)3 Zeta

EYDVLDKRRGRDPEMGGKPRRKNPQEGLYNELQKDKMAEAYSEIGMKGERRRGKGHDGL
YQGLSTATKDTYDALHMQALPPR

FIG. 14C tTA

```
  1  MSRLDKSKVI NSALELLNEV GIEGLTTRKL AQKLGVEQPT LYWHVKNKRA
 51  LLDALAIEML DRHHTHFCPL EGESWQDFLR NNAKSFRCAL LSHRDGAKVH
101  LGTRPTEKQY ETLENQLAFL CQQGFSLENA LYALSAVGHF TLGCVLEDQE
151  HQVAKEERET PTTDSMPPLL RQAIELFDHQ GAEPAFLFGL ELIICGLEKQ
201  LKCESGGPAD ALDDFDLDML PADALDDFDL DMLPADALDD LDLDMLPG
```

FIG. 15A tTA-T2A-CD19t

```
  1  MSRLDKSKVI NSALELLNEV GIEGLTTRKL AQKLGVEQPT LYWHVKNKRA
     tTA

 51  LLDALAIEML DRHHTHFCPL EGESWQDFLR NNAKSFRCAL LSHRDGAKVH
101  LGTRPTEKQY ETLENQLAFL CQQGFSLENA LYALSAVGHF TLGCVLEDQE
151  HQVAKEERET PTTDSMPPLL RQAIELFDHQ GAEPAFLFGL ELIICGLEKQ
201  LKCESGGPAD ALDDFDLDML PADALDDFDL DMLPADALDD LDLDMLPGLE
                                                      T2A

251  GGGEGRGSLL TCGDVEENPG PRMPPPRLLF FLLFLTPMEV RPEEPLVVKV
                          CD19t

301  EEGDNAVLQC LKGTSDGPTQ QLTWSRESPL KPFLKLSLGL PGLGIHMRPL
351  AIWLFIFNVS QQMGGFYLCQ PGPPSEKAWQ PGWTVNVEGS GELFRWNVSD
401  LGGLGCGLKN RSSEGPSSPS GKLMSPKLYV WAKDRPEIWE GEPPCVPPRD
451  SLNQSLSQDL TMAPGSTLWL SCGVPPDSVS RGPLSWTHVH PKGPKSLLSL
501  ELKDDRPARD MWVMETGLLL PRATAQDAGK YYCHRGNLTM SFHLEITARP
551  VLWHWLLRTG GWKVSAVTLA YLIFCLCSLV GILHLQRALV LRRKR
```

FIG. 15B

SEQUENCE LISTING

```
<160> NUMBER OF SEQ ID NOS: 48

<210> SEQ ID NO 1
<211> LENGTH: 246
<212> TYPE: PRT
<213> ORGANISM: Artificial
<220> FEATURE:
<223> OTHER INFORMATION: huCCR4 scFv

<400> SEQUENCE: 1

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Gly Ser Thr Ser Gly Gly Gly Ser Gly Gly Gly Ser Gly
        115                 120                 125

Gly Gly Gly Ser Ser Asp Ile Val Met Ser Gln Ser Pro Asp Ser Leu
    130                 135                 140

Ala Val Ser Leu Gly Glu Arg Val Thr Leu Asn Cys Lys Ser Ser Gln
145                 150                 155                 160

Ser Leu Leu Tyr Ser Gly Asn Gln Lys Asn Tyr Leu Ala Trp Tyr Gln
                165                 170                 175

Gln Lys Pro Gly Gln Ser Pro Lys Leu Leu Ile Tyr Trp Ala Ser Ala
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Val Gln Ala Glu Asp Val Ala Val
    210                 215                 220

Tyr Tyr Cys Gln Gln Tyr Tyr Ser Tyr Pro Leu Thr Phe Gly Ala Gly
225                 230                 235                 240

Thr Lys Leu Glu Leu Lys
                245


<210> SEQ ID NO 2
<211> LENGTH: 10
<212> TYPE: PRT
<213> ORGANISM: Artificial
```

<220> FEATURE:
<223> OTHER INFORMATION: linker

<400> SEQUENCE: 2

Gly Gly Gly Ser Ser Gly Gly Gly Ser Gly
1 5 10

<210> SEQ ID NO 3
<211> LENGTH: 12
<212> TYPE: PRT
<213> ORGANISM: Artificial
<220> FEATURE:
<223> OTHER INFORMATION: IgG4 hinge (S228P)

<400> SEQUENCE: 3

Glu Ser Lys Tyr Gly Pro Pro Cys Pro Pro Cys Pro
1 5 10

<210> SEQ ID NO 4
<211> LENGTH: 12
<212> TYPE: PRT
<213> ORGANISM: Artificial
<220> FEATURE:
<223> OTHER INFORMATION: IgG4 hinge

<400> SEQUENCE: 4

Glu Ser Lys Tyr Gly Pro Pro Cys Pro Ser Cys Pro
1 5 10

<210> SEQ ID NO 5
<211> LENGTH: 22
<212> TYPE: PRT
<213> ORGANISM: Artificial
<220> FEATURE:
<223> OTHER INFORMATION: IgG4 hinge (S228P)+ linker

<400> SEQUENCE: 5

Glu Ser Lys Tyr Gly Pro Pro Cys Pro Pro Cys Pro Gly Gly Gly Ser
1 5 10 15

Ser Gly Gly Gly Ser Gly
20

<210> SEQ ID NO 6
<211> LENGTH: 39
<212> TYPE: PRT
<213> ORGANISM: Artificial
<220> FEATURE:
<223> OTHER INFORMATION: CD28 hinge

<400> SEQUENCE: 6

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro
35

<210> SEQ ID NO 7
<211> LENGTH: 48
<212> TYPE: PRT
<213> ORGANISM: Artificial
<220> FEATURE:
<223> OTHER INFORMATION: CD8 hinge-48aa

<400> SEQUENCE: 7

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45


<210> SEQ ID NO 8
<211> LENGTH: 45
<212> TYPE: PRT
<213> ORGANISM: Artificial
<220> FEATURE:
<223> OTHER INFORMATION: CD8 hinge-45aa

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 9
<211> LENGTH: 129
<212> TYPE: PRT
<213> ORGANISM: Artificial
<220> FEATURE:
<223> OTHER INFORMATION: IgG4(HL-CH3) (S228P)

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys


<210> SEQ ID NO 10
<211> LENGTH: 229
<212> TYPE: PRT
<213> ORGANISM: Artificial
<220> FEATURE:
<223> OTHER INFORMATION: IgG4(L235E,N297Q)

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 11
<211> LENGTH: 229
<212> TYPE: PRT
<213> ORGANISM: Artificial
<220> FEATURE:
<223> OTHER INFORMATION: IgG4(S228P, L235E,N297Q)

<400> SEQUENCE: 11

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160
```

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 12
<211> LENGTH: 107
<212> TYPE: PRT
<213> ORGANISM: Artificial
<220> FEATURE:
<223> OTHER INFORMATION: IgG4(CH3)

<400> SEQUENCE: 12

Gly Gln Pro Arg Glu Pro Gln Val Tyr Thr Leu Pro Pro Ser Gln Glu
1 5 10 15

Glu Met Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Arg Leu Thr Val Asp Lys Ser Arg Trp Gln Glu Gly
65 70 75 80

Asn Val Phe Ser Cys Ser Val Met His Glu Ala Leu His Asn His Tyr
85 90 95

Thr Gln Lys Ser Leu Ser Leu Ser Leu Gly Lys
100 105

<210> SEQ ID NO 13
<211> LENGTH: 21
<212> TYPE: PRT
<213> ORGANISM: Artificial
<220> FEATURE:
<223> OTHER INFORMATION: CD3z

<400> SEQUENCE: 13

Leu Cys Tyr Leu Leu Asp Gly Ile Leu Phe Ile Tyr Gly Val Ile Leu
1 5 10 15

Thr Ala Leu Phe Leu
20

<210> SEQ ID NO 14
<211> LENGTH: 27
<212> TYPE: PRT
<213> ORGANISM: Artificial
<220> FEATURE:
<223> OTHER INFORMATION: CD28

<400> SEQUENCE: 14

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 15
<211> LENGTH: 28
<212> TYPE: PRT
<213> ORGANISM: Artificial
<220> FEATURE:
<223> OTHER INFORMATION: CD28(M)

<400> SEQUENCE: 15

```
Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25
```

<210> SEQ ID NO 16
<211> LENGTH: 22
<212> TYPE: PRT
<213> ORGANISM: Artificial
<220> FEATURE:
<223> OTHER INFORMATION: CD4

<400> SEQUENCE: 16

```
Met Ala Leu Ile Val Leu Gly Gly Val Ala Gly Leu Leu Leu Phe Ile
1               5                   10                  15

Gly Leu Gly Ile Phe Phe
            20
```

<210> SEQ ID NO 17
<211> LENGTH: 21
<212> TYPE: PRT
<213> ORGANISM: Artificial
<220> FEATURE:
<223> OTHER INFORMATION: CD8tm

<400> SEQUENCE: 17

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 18
<211> LENGTH: 23
<212> TYPE: PRT
<213> ORGANISM: Artificial
<220> FEATURE:
<223> OTHER INFORMATION: CD8tm2

<400> SEQUENCE: 18

```
Ile Tyr Ile Trp Ala Pro Leu Ala Gly Thr Cys Gly Val Leu Leu Leu
1               5                   10                  15

Ser Leu Val Ile Thr Leu Tyr
            20
```

<210> SEQ ID NO 19
<211> LENGTH: 24
<212> TYPE: PRT
<213> ORGANISM: Artificial
<220> FEATURE:
<223> OTHER INFORMATION: CD8tm3

<400> SEQUENCE: 19

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 20
<211> LENGTH: 27
<212> TYPE: PRT
<213> ORGANISM: Artificial
<220> FEATURE:
<223> OTHER INFORMATION: 41BB

<400> SEQUENCE: 20

Ile Ile Ser Phe Phe Leu Ala Leu Thr Ser Thr Ala Leu Leu Phe Leu
1 5 10 15

Leu Phe Phe Leu Thr Leu Arg Phe Ser Val Val
20 25

<210> SEQ ID NO 21
<211> LENGTH: 112
<212> TYPE: PRT
<213> ORGANISM: Artificial
<220> FEATURE:
<223> OTHER INFORMATION: CD3 Zeta

<400> SEQUENCE: 21

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 22
<211> LENGTH: 41
<212> TYPE: PRT
<213> ORGANISM: Artificial
<220> FEATURE:
<223> OTHER INFORMATION: CD28

<400> SEQUENCE: 22

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 23
<211> LENGTH: 41
<212> TYPE: PRT
<213> ORGANISM: Artificial
<220> FEATURE:
<223> OTHER INFORMATION: CD28gg

<400> SEQUENCE: 23

Arg Ser Lys Arg Ser Arg Gly Gly His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 24
<211> LENGTH: 42
<212> TYPE: PRT
<213> ORGANISM: Artificial
<220> FEATURE:
<223> OTHER INFORMATION: 41BB

<400> SEQUENCE: 24

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 25
<211> LENGTH: 42
<212> TYPE: PRT
<213> ORGANISM: Artificial
<220> FEATURE:
<223> OTHER INFORMATION: OX40

<400> SEQUENCE: 25

Ala Leu Tyr Leu Leu Arg Arg Asp Gln Arg Leu Pro Pro Asp Ala His
1 5 10 15

Lys Pro Pro Gly Gly Gly Ser Phe Arg Thr Pro Ile Gln Glu Glu Gln
20 25 30

Ala Asp Ala His Ser Thr Leu Ala Lys Ile
35 40

<210> SEQ ID NO 26
<211> LENGTH: 323
<212> TYPE: PRT
<213> ORGANISM: Artificial
<220> FEATURE:
<223> OTHER INFORMATION: truncated CD19R

<400> SEQUENCE: 26

Met Pro Pro Pro Arg Leu Leu Phe Phe Leu Leu Phe Leu Thr Pro Met
1 5 10 15

Glu Val Arg Pro Glu Glu Pro Leu Val Val Lys Val Glu Glu Gly Asp
20 25 30

Asn Ala Val Leu Gln Cys Leu Lys Gly Thr Ser Asp Gly Pro Thr Gln
35 40 45

Gln Leu Thr Trp Ser Arg Glu Ser Pro Leu Lys Pro Phe Leu Lys Leu
50 55 60

Ser Leu Gly Leu Pro Gly Leu Gly Ile His Met Arg Pro Leu Ala Ile
65 70 75 80

Trp Leu Phe Ile Phe Asn Val Ser Gln Gln Met Gly Gly Phe Tyr Leu
85 90 95

Cys Gln Pro Gly Pro Pro Ser Glu Lys Ala Trp Gln Pro Gly Trp Thr
100 105 110

Val Asn Val Glu Gly Ser Gly Glu Leu Phe Arg Trp Asn Val Ser Asp
115 120 125

```
Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg


<210> SEQ ID NO 27
<211> LENGTH: 24
<212> TYPE: PRT
<213> ORGANISM: Artificial
<220> FEATURE:
<223> OTHER INFORMATION: ribosomal skip sequence

<400> SEQUENCE: 27

Leu Glu Gly Gly Gly Glu Gly Arg Gly Ser Leu Leu Thr Cys Gly Asp
1               5                   10                  15

Val Glu Glu Asn Pro Gly Pro Arg
            20


<210> SEQ ID NO 28
<211> LENGTH: 354
<212> TYPE: PRT
<213> ORGANISM: Artificial
<220> FEATURE:
<223> OTHER INFORMATION: truncated EGFR

<400> SEQUENCE: 28

Leu Val Thr Ser Leu Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
            20                  25                  30

Asp Ser Leu Ser Ile Asn Ala Thr Asn Ile Lys His Phe Lys Asn Cys
        35                  40                  45

Thr Ser Ile Ser Gly Asp Leu His Ile Leu Pro Val Ala Phe Arg Gly
    50                  55                  60

Asp Ser Phe Thr His Thr Pro Pro Leu Asp Pro Gln Glu Leu Asp Ile
65                  70                  75                  80
```

Leu Lys Thr Val Lys Glu Ile Thr Gly Phe Leu Leu Ile Gln Ala Trp
85 90 95

Pro Glu Asn Arg Thr Asp Leu His Ala Phe Glu Asn Leu Glu Ile Ile
100 105 110

Arg Gly Arg Thr Lys Gln His Gly Gln Phe Ser Leu Ala Val Val Ser
115 120 125

Leu Asn Ile Thr Ser Leu Gly Leu Arg Ser Leu Lys Glu Ile Ser Asp
130 135 140

Gly Asp Val Ile Ile Ser Gly Asn Lys Asn Leu Cys Tyr Ala Asn Thr
145 150 155 160

Ile Asn Trp Lys Lys Leu Phe Gly Thr Ser Gly Gln Lys Thr Lys Ile
165 170 175

Ile Ser Asn Arg Gly Glu Asn Ser Cys Lys Ala Thr Gly Gln Val Cys
180 185 190

His Ala Leu Cys Ser Pro Glu Gly Cys Trp Gly Pro Glu Pro Arg Asp
195 200 205

Cys Val Ser Cys Arg Asn Val Ser Arg Gly Arg Glu Cys Val Asp Lys
210 215 220

Cys Asn Leu Leu Glu Gly Glu Pro Arg Glu Phe Val Glu Asn Ser Glu
225 230 235 240

Cys Ile Gln Cys His Pro Glu Cys Leu Pro Gln Ala Met Asn Ile Thr
245 250 255

Cys Thr Gly Arg Gly Pro Asp Asn Cys Ile Gln Cys Ala His Tyr Ile
260 265 270

Asp Gly Pro His Cys Val Lys Thr Cys Pro Ala Gly Val Met Gly Glu
275 280 285

Asn Asn Thr Leu Val Trp Lys Tyr Ala Asp Ala Gly His Val Cys His
290 295 300

Leu Cys His Pro Asn Cys Thr Tyr Gly Cys Thr Gly Pro Gly Leu Glu
305 310 315 320

Gly Cys Pro Thr Asn Gly Pro Lys Ile Pro Ser Ile Ala Thr Gly Met
325 330 335

Val Gly Ala Leu Leu Leu Leu Leu Val Val Ala Leu Gly Ile Gly Leu
340 345 350

Phe Met

<210> SEQ ID NO 29
<211> LENGTH: 456
<212> TYPE: PRT
<213> ORGANISM: Artificial
<220> FEATURE:
<223> OTHER INFORMATION: CCR4scFv-Linker-CD4tm-41BB-Zeta with GMCSFRa signal sequence

<400> SEQUENCE: 29

Met Leu Leu Leu Val Thr Ser Leu Leu Leu Cys Glu Leu Pro His Pro
1 5 10 15

Ala Phe Leu Leu Ile Pro Gln Val Gln Leu Val Gln Ser Gly Ala Glu
20 25 30

Val Lys Lys Pro Gly Ala Ser Val Lys Val Ser Cys Lys Ala Ser Gly
35 40 45

Tyr Thr Phe Ala Ser Tyr Tyr Met His Trp Met Arg Gln Ala Pro Gly
50 55 60

Gln Gly Leu Glu Trp Ile Gly Trp Ile Asn Pro Gly Asn Val Asn Thr
65 70 75 80

```
Lys Tyr Asn Glu Lys Phe Lys Gly Arg Ala Thr Leu Thr Val Asp Thr
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Ser Thr Tyr Tyr Arg Pro Leu Asp
        115                 120                 125

Tyr Trp Gly Gln Gly Thr Leu Val Thr Val Ser Ser Ser Gly Gly Gly
    130                 135                 140

Ser Gly Gly Gly Gly Ser Gly Gly Gly Gly Ser Asp Ile Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Ile Leu Tyr Ser Ser Asn Gln Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Thr Arg Glu Ser Gly Val Pro Asp Arg Phe Ser
    210                 215                 220

Gly Ser Gly Ser Gly Thr Asp Phe Thr Leu Thr Ile Ser Ser Leu Gln
225                 230                 235                 240

Ala Glu Asp Val Ala Val Tyr Tyr Cys His Gln Tyr Leu Ser Ser Tyr
                245                 250                 255

Thr Phe Gly Gln Gly Thr Lys Leu Glu Ile Lys Gly Gly Gly Ser Ser
            260                 265                 270

Gly Gly Gly Ser Gly Met Ala Leu Ile Val Leu Gly Gly Val Ala Gly
        275                 280                 285

Leu Leu Leu Phe Ile Gly Leu Gly Ile Phe Phe Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Gly Gly Gly Arg Val Lys Phe Ser Arg Ser Ala
            340                 345                 350

Asp Ala Pro Ala Tyr Gln Gln Gly Gln Asn Gln Leu Tyr Asn Glu Leu
        355                 360                 365

Asn Leu Gly Arg Arg Glu Glu Tyr Asp Val Leu Asp Lys Arg Arg Gly
    370                 375                 380

Arg Asp Pro Glu Met Gly Gly Lys Pro Arg Arg Lys Asn Pro Gln Glu
385                 390                 395                 400

Gly Leu Tyr Asn Glu Leu Gln Lys Asp Lys Met Ala Glu Ala Tyr Ser
                405                 410                 415

Glu Ile Gly Met Lys Gly Glu Arg Arg Arg Gly Lys Gly His Asp Gly
            420                 425                 430

Leu Tyr Gln Gly Leu Ser Thr Ala Thr Lys Asp Thr Tyr Asp Ala Leu
        435                 440                 445

His Met Gln Ala Leu Pro Pro Arg
    450                 455
```

<210> SEQ ID NO 30
<211> LENGTH: 675
<212> TYPE: PRT
<213> ORGANISM: Artificial
<220> FEATURE:
<223> OTHER INFORMATION: CCR4scFv-IgG4(L235E,N297Q)-CD4tm-41BB-Zeta with GMCSFRa signal sequence

<400> SEQUENCE: 30

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Ala Ser Tyr Tyr Met His Trp Met Arg Gln Ala Pro Gly
    50                  55                  60

Gln Gly Leu Glu Trp Ile Gly Trp Ile Asn Pro Gly Asn Val Asn Thr
65                  70                  75                  80

Lys Tyr Asn Glu Lys Phe Lys Gly Arg Ala Thr Leu Thr Val Asp Thr
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Ser Thr Tyr Tyr Arg Pro Leu Asp
        115                 120                 125

Tyr Trp Gly Gln Gly Thr Leu Val Thr Val Ser Ser Ser Gly Gly Gly
    130                 135                 140

Ser Gly Gly Gly Gly Ser Gly Gly Gly Gly Ser Asp Ile Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Ile Leu Tyr Ser Ser Asn Gln Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Thr Arg Glu Ser Gly Val Pro Asp Arg Phe Ser
    210                 215                 220

Gly Ser Gly Ser Gly Thr Asp Phe Thr Leu Thr Ile Ser Ser Leu Gln
225                 230                 235                 240

Ala Glu Asp Val Ala Val Tyr Tyr Cys His Gln Tyr Leu Ser Ser Tyr
                245                 250                 255

Thr Phe Gly Gln Gly Thr Lys Leu Glu Ile Lys Glu Ser Lys Tyr Gly
            260                 265                 270

Pro Pro Cys Pro Pro Cys Pro Ala Pro Glu Phe Glu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser Gln Glu Asp Pro
305                 310                 315                 320

Glu Val Gln Phe Asn Trp Tyr Val Asp Gly Val Glu Val His Asn Ala
                325                 330                 335

Lys Thr Lys Pro Arg Glu Glu Gln Phe Gln Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Gly Leu Pro Ser Ser Ile Glu Lys Thr
    370                 375                 380

Ile Ser Lys Ala Lys Gly Gln Pro Arg Glu Pro Gln Val Tyr Thr Leu
385                 390                 395                 400
```

```
Pro Pro Ser Gln Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Arg Leu Thr Val Asp Lys Ser
    450                 455                 460

Arg Trp Gln Glu Gly Asn Val Phe Ser Cys Ser Val Met His Glu Ala
465                 470                 475                 480

Leu His Asn His Tyr Thr Gln Lys Ser Leu Ser Leu Ser Leu Gly Lys
                485                 490                 495

Met Ala Leu Ile Val Leu Gly Gly Val Ala Gly Leu Leu Leu Phe Ile
            500                 505                 510

Gly Leu Gly Ile Phe Phe Lys Arg Gly Arg Lys Lys Leu Leu Tyr Ile
        515                 520                 525

Phe Lys Gln Pro Phe Met Arg Pro Val Gln Thr Thr Gln Glu Glu Asp
    530                 535                 540

Gly Cys Ser Cys Arg Phe Pro Glu Glu Glu Glu Gly Gly Cys Glu Leu
545                 550                 555                 560

Gly Gly Gly Arg Val Lys Phe Ser Arg Ser Ala Asp Ala Pro Ala Tyr
                565                 570                 575

Gln Gln Gly Gln Asn Gln Leu Tyr Asn Glu Leu Asn Leu Gly Arg Arg
            580                 585                 590

Glu Glu Tyr Asp Val Leu Asp Lys Arg Arg Gly Arg Asp Pro Glu Met
        595                 600                 605

Gly Gly Lys Pro Arg Arg Lys Asn Pro Gln Glu Gly Leu Tyr Asn Glu
    610                 615                 620

Leu Gln Lys Asp Lys Met Ala Glu Ala Tyr Ser Glu Ile Gly Met Lys
625                 630                 635                 640

Gly Glu Arg Arg Arg Gly Lys Gly His Asp Gly Leu Tyr Gln Gly Leu
                645                 650                 655

Ser Thr Ala Thr Lys Asp Thr Tyr Asp Ala Leu His Met Gln Ala Leu
            660                 665                 670

Pro Pro Arg
        675
```

<210> SEQ ID NO 31
<211> LENGTH: 575
<212> TYPE: PRT
<213> ORGANISM: Artificial
<220> FEATURE:
<223> OTHER INFORMATION: CCR4scFv-IgG4(HL-CH3)-CD4tm-41BB-Zeta with GMCSFRa signal sequence

<400> SEQUENCE: 31

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Ala Ser Tyr Tyr Met His Trp Met Arg Gln Ala Pro Gly
    50                  55                  60

Gln Gly Leu Glu Trp Ile Gly Trp Ile Asn Pro Gly Asn Val Asn Thr
65                  70                  75                  80
```

```
Lys Tyr Asn Glu Lys Phe Lys Gly Arg Ala Thr Leu Thr Val Asp Thr
                85                  90                  95

Ser Thr Asn Thr Ala Tyr Met Glu Leu Ser Ser Leu Arg Ser Glu Asp
            100                 105                 110

Thr Ala Val Tyr Tyr Cys Ala Arg Ser Thr Tyr Tyr Arg Pro Leu Asp
        115                 120                 125

Tyr Trp Gly Gln Gly Thr Leu Val Thr Val Ser Ser Ser Gly Gly Gly
    130                 135                 140

Ser Gly Gly Gly Gly Ser Gly Gly Gly Gly Ser Asp Ile Val Met Thr
145                 150                 155                 160

Gln Ser Pro Asp Ser Leu Ala Val Ser Leu Gly Glu Arg Ala Thr Ile
                165                 170                 175

Asn Cys Lys Ser Ser Gln Ser Ile Leu Tyr Ser Ser Asn Gln Lys Asn
            180                 185                 190

Tyr Leu Ala Trp Tyr Gln Gln Lys Pro Gly Gln Ser Pro Lys Leu Leu
        195                 200                 205

Ile Tyr Trp Ala Ser Thr Arg Glu Ser Gly Val Pro Asp Arg Phe Ser
    210                 215                 220

Gly Ser Gly Ser Gly Thr Asp Phe Thr Leu Thr Ile Ser Ser Leu Gln
225                 230                 235                 240

Ala Glu Asp Val Ala Val Tyr Tyr Cys His Gln Tyr Leu Ser Ser Tyr
                245                 250                 255

Thr Phe Gly Gln Gly Thr Lys Leu Glu Ile Lys Glu Ser Lys Tyr Gly
            260                 265                 270

Pro Pro Cys Pro Pro Cys Pro Gly Gly Gly Ser Ser Gly Gly Gly Ser
        275                 280                 285

Gly Gly Gln Pro Arg Glu Pro Gln Val Tyr Thr Leu Pro Pro Ser Gln
    290                 295                 300

Glu Glu Met Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Arg Leu Thr Val Asp Lys Ser Arg Trp Gln Glu
        355                 360                 365

Gly Asn Val Phe Ser Cys Ser Val Met His Glu Ala Leu His Asn His
    370                 375                 380

Tyr Thr Gln Lys Ser Leu Ser Leu Ser Leu Gly Lys Met Ala Leu Ile
385                 390                 395                 400

Val Leu Gly Gly Val Ala Gly Leu Leu Leu Phe Ile Gly Leu Gly Ile
                405                 410                 415

Phe Phe Lys Arg Gly Arg Lys Lys Leu Leu Tyr Ile Phe Lys Gln Pro
            420                 425                 430

Phe Met Arg Pro Val Gln Thr Thr Gln Glu Glu Asp Gly Cys Ser Cys
        435                 440                 445

Arg Phe Pro Glu Glu Glu Glu Gly Gly Cys Glu Leu Gly Gly Gly Arg
    450                 455                 460

Val Lys Phe Ser Arg Ser Ala Asp Ala Pro Ala Tyr Gln Gln Gly Gln
465                 470                 475                 480

Asn Gln Leu Tyr Asn Glu Leu Asn Leu Gly Arg Arg Glu Glu Tyr Asp
                485                 490                 495
```

```
Val Leu Asp Lys Arg Arg Gly Arg Asp Pro Glu Met Gly Gly Lys Pro
            500                 505                 510

Arg Arg Lys Asn Pro Gln Glu Gly Leu Tyr Asn Glu Leu Gln Lys Asp
        515                 520                 525

Lys Met Ala Glu Ala Tyr Ser Glu Ile Gly Met Lys Gly Glu Arg Arg
    530                 535                 540

Arg Gly Lys Gly His Asp Gly Leu Tyr Gln Gly Leu Ser Thr Ala Thr
545                 550                 555                 560

Lys Asp Thr Tyr Asp Ala Leu His Met Gln Ala Leu Pro Pro Arg
                565                 570                 575


<210> SEQ ID NO 32
<211> LENGTH: 118
<212> TYPE: PRT
<213> ORGANISM: Artificial
<220> FEATURE:
<223> OTHER INFORMATION: huCCR4 scFv V

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser
        115


<210> SEQ ID NO 33
<211> LENGTH: 112
<212> TYPE: PRT
<213> ORGANISM: Artificial
<220> FEATURE:
<223> OTHER INFORMATION: huCCR4 scFv V

<400> SEQUENCE: 33

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
            100                 105                 110
```

<210> SEQ ID NO 34
<211> LENGTH: 118
<212> TYPE: PRT
<213> ORGANISM: Artificial
<220> FEATURE:
<223> OTHER INFORMATION: huCCR4 scFv V

<400> SEQUENCE: 34

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Gln
20 25 30

Trp Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Ser Thr Trp Tyr Arg Pro Leu Asp Tyr Trp Gly Gln Gly Thr
100 105 110

Leu Val Thr Val Ser Ser
115

<210> SEQ ID NO 35
<211> LENGTH: 112
<212> TYPE: PRT
<213> ORGANISM: Artificial
<220> FEATURE:
<223> OTHER INFORMATION: huCCR4 scFv V

<400> SEQUENCE: 35

Asp Ile Val Met Thr Gln Ser Pro Asp Ser Leu Ala Val Ser Leu Gly
1 5 10 15

Glu Arg Ala Thr Met Ser Cys Lys Ser Ser Gln Ser Ile Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys His Gln
85 90 95

Tyr Ile Ser Ser Tyr Thr Phe Gly Gln Gly Thr Lys Leu Glu Ile Lys
100 105 110

<210> SEQ ID NO 36
<211> LENGTH: 118
<212> TYPE: PRT
<213> ORGANISM: Artificial
<220> FEATURE:
<223> OTHER INFORMATION: huCCR4 scFv V

<400> SEQUENCE: 36

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Ala
20 25 30

Trp Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Ser Thr Tyr Tyr Arg Pro Leu Asp Tyr Trp Gly Gln Gly Thr
100 105 110

Leu Val Thr Val Ser Ser
115

<210> SEQ ID NO 37
<211> LENGTH: 112
<212> TYPE: PRT
<213> ORGANISM: Artificial
<220> FEATURE:
<223> OTHER INFORMATION: huCCR4 scFv V

<400> SEQUENCE: 37

Asp Ile Val Met Thr Gln Ser Pro Asp Ser Leu Ala Val Ser Leu Gly
1 5 10 15

Glu Arg Ala Thr Met Ser Cys Lys Ser Ser Gln Ser Ile Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys His Gln
85 90 95

Tyr Met Ser Ser Tyr Thr Phe Gly Gln Gly Thr Lys Leu Glu Ile Lys
100 105 110

<210> SEQ ID NO 38
<211> LENGTH: 434
<212> TYPE: PRT
<213> ORGANISM: Artificial
<220> FEATURE:
<223> OTHER INFORMATION: CCR4scFv-Linker-CD4tm-41BB-Zeta

<400> SEQUENCE: 38

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Tyr
20 25 30

Tyr Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Ser Thr Tyr Tyr Arg Pro Leu Asp Tyr Trp Gly Gln Gly Thr
100 105 110

Leu Val Thr Val Ser Ser Ser Gly Gly Gly Ser Gly Gly Gly Gly Ser
115 120 125

Gly Gly Gly Gly Ser Asp Ile Val Met Thr Gln Ser Pro Asp Ser Leu
130 135 140

Ala Val Ser Leu Gly Glu Arg Ala Thr Ile Asn Cys Lys Ser Ser Gln
145 150 155 160

Ser Ile Leu Tyr Ser Ser Asn Gln Lys Asn Tyr Leu Ala Trp Tyr Gln
165 170 175

Gln Lys Pro Gly Gln Ser Pro Lys Leu Leu Ile Tyr Trp Ala Ser Thr
180 185 190

Arg Glu Ser Gly Val Pro Asp Arg Phe Ser Gly Ser Gly Ser Gly Thr
195 200 205

Asp Phe Thr Leu Thr Ile Ser Ser Leu Gln Ala Glu Asp Val Ala Val
210 215 220

Tyr Tyr Cys His Gln Tyr Leu Ser Ser Tyr Thr Phe Gly Gln Gly Thr
225 230 235 240

Lys Leu Glu Ile Lys Gly Gly Gly Ser Ser Gly Gly Gly Ser Gly Met
245 250 255

Ala Leu Ile Val Leu Gly Gly Val Ala Gly Leu Leu Leu Phe Ile Gly
260 265 270

Leu Gly Ile Phe Phe Lys Arg Gly Arg Lys Lys Leu Leu Tyr Ile Phe
275 280 285

Lys Gln Pro Phe Met Arg Pro Val Gln Thr Thr Gln Glu Glu Asp Gly
290 295 300

Cys Ser Cys Arg Phe Pro Glu Glu Glu Glu Gly Gly Cys Glu Leu Gly
305 310 315 320

Gly Gly Arg Val Lys Phe Ser Arg Ser Ala Asp Ala Pro Ala Tyr Gln
325 330 335

Gln Gly Gln Asn Gln Leu Tyr Asn Glu Leu Asn Leu Gly Arg Arg Glu
340 345 350

Glu Tyr Asp Val Leu Asp Lys Arg Arg Gly Arg Asp Pro Glu Met Gly
355 360 365

Gly Lys Pro Arg Arg Lys Asn Pro Gln Glu Gly Leu Tyr Asn Glu Leu
370 375 380

Gln Lys Asp Lys Met Ala Glu Ala Tyr Ser Glu Ile Gly Met Lys Gly
385 390 395 400

Glu Arg Arg Arg Gly Lys Gly His Asp Gly Leu Tyr Gln Gly Leu Ser
405 410 415

Thr Ala Thr Lys Asp Thr Tyr Asp Ala Leu His Met Gln Ala Leu Pro
420 425 430

Pro Arg

<210> SEQ ID NO 39
<211> LENGTH: 653
<212> TYPE: PRT
<213> ORGANISM: Artificial
<220> FEATURE:
<223> OTHER INFORMATION: CCR4scFv-IgG4(L235E,N297Q)-CD4tm-41BB-Zeta

<400> SEQUENCE: 39

Gln Val Gln Leu Val Gln Ser Gly Ala Glu Val Lys Lys Pro Gly Ala
1 5 10 15

-continued

```
Ser Val Lys Val Ser Cys Lys Ala Ser Gly Tyr Thr Phe Ala Ser Tyr
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser Ser Gly Gly Gly Ser Gly Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Ile Leu Tyr Ser Ser Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys His Gln Tyr Leu Ser Ser Tyr Thr Phe Gly Gln Gly Thr
225                 230                 235                 240

Lys Leu Glu Ile Lys Glu Ser Lys Tyr Gly Pro Pro Cys Pro Pro Cys
                245                 250                 255

Pro Ala Pro Glu Phe Glu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Gln Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
```

435 440 445

Val Phe Ser Cys Ser Val Met His Glu Ala Leu His Asn His Tyr Thr
450 455 460

Gln Lys Ser Leu Ser Leu Ser Leu Gly Lys Met Ala Leu Ile Val Leu
465 470 475 480

Gly Gly Val Ala Gly Leu Leu Leu Phe Ile Gly Leu Gly Ile Phe Phe
485 490 495

Lys Arg Gly Arg Lys Lys Leu Leu Tyr Ile Phe Lys Gln Pro Phe Met
500 505 510

Arg Pro Val Gln Thr Thr Gln Glu Glu Asp Gly Cys Ser Cys Arg Phe
515 520 525

Pro Glu Glu Glu Glu Gly Gly Cys Glu Leu Gly Gly Gly Arg Val Lys
530 535 540

Phe Ser Arg Ser Ala Asp Ala Pro Ala Tyr Gln Gln Gly Gln Asn Gln
545 550 555 560

Leu Tyr Asn Glu Leu Asn Leu Gly Arg Arg Glu Glu Tyr Asp Val Leu
565 570 575

Asp Lys Arg Arg Gly Arg Asp Pro Glu Met Gly Gly Lys Pro Arg Arg
580 585 590

Lys Asn Pro Gln Glu Gly Leu Tyr Asn Glu Leu Gln Lys Asp Lys Met
595 600 605

Ala Glu Ala Tyr Ser Glu Ile Gly Met Lys Gly Glu Arg Arg Arg Gly
610 615 620

Lys Gly His Asp Gly Leu Tyr Gln Gly Leu Ser Thr Ala Thr Lys Asp
625 630 635 640

Thr Tyr Asp Ala Leu His Met Gln Ala Leu Pro Pro Arg
645 650

<210> SEQ ID NO 40
<211> LENGTH: 553
<212> TYPE: PRT
<213> ORGANISM: Artificial
<220> FEATURE:
<223> OTHER INFORMATION: CCR4scFv-IgG4(HL-CH3)-CD4tm-41BB-Zeta

<400> SEQUENCE: 40

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Tyr
20 25 30

Tyr Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Ser Thr Tyr Tyr Arg Pro Leu Asp Tyr Trp Gly Gln Gly Thr
100 105 110

Leu Val Thr Val Ser Ser Ser Gly Gly Gly Ser Gly Gly Gly Gly Ser
115 120 125

Gly Gly Gly Gly Ser Asp Ile Val Met Thr Gln Ser Pro Asp Ser Leu
130 135 140

Ala Val Ser Leu Gly Glu Arg Ala Thr Ile Asn Cys Lys Ser Ser Gln 145 150 155 160

Ser Ile Leu Tyr Ser Ser Asn Gln Lys Asn Tyr Leu Ala Trp Tyr Gln
165 170 175

Gln Lys Pro Gly Gln Ser Pro Lys Leu Leu Ile Tyr Trp Ala Ser Thr
180 185 190

Arg Glu Ser Gly Val Pro Asp Arg Phe Ser Gly Ser Gly Ser Gly Thr
195 200 205

Asp Phe Thr Leu Thr Ile Ser Ser Leu Gln Ala Glu Asp Val Ala Val
210 215 220

Tyr Tyr Cys His Gln Tyr Leu Ser Ser Tyr Thr Phe Gly Gln Gly Thr
225 230 235 240

Lys Leu Glu Ile Lys Glu Ser Lys Tyr Gly Pro Pro Cys Pro Pro Cys
245 250 255

Pro Gly Gly Gly Ser Ser Gly Gly Gly Ser Gly Gly Gln Pro Arg Glu
260 265 270

Pro Gln Val Tyr Thr Leu Pro Pro Ser Gln Glu Glu Met Thr Lys Asn
275 280 285

Gln Val Ser Leu Thr Cys Leu Val Lys Gly Phe Tyr Pro Ser Asp Ile
290 295 300

Ala Val Glu Trp Glu Ser Asn Gly Gln Pro Glu Asn Asn Tyr Lys Thr
305 310 315 320

Thr Pro Pro Val Leu Asp Ser Asp Gly Ser Phe Phe Leu Tyr Ser Arg
325 330 335

Leu Thr Val Asp Lys Ser Arg Trp Gln Glu Gly Asn Val Phe Ser Cys
340 345 350

Ser Val Met His Glu Ala Leu His Asn His Tyr Thr Gln Lys Ser Leu
355 360 365

Ser Leu Ser Leu Gly Lys Met Ala Leu Ile Val Leu Gly Gly Val Ala
370 375 380

Gly Leu Leu Leu Phe Ile Gly Leu Gly Ile Phe Phe Lys Arg Gly Arg
385 390 395 400

Lys Lys Leu Leu Tyr Ile Phe Lys Gln Pro Phe Met Arg Pro Val Gln
405 410 415

Thr Thr Gln Glu Glu Asp Gly Cys Ser Cys Arg Phe Pro Glu Glu Glu
420 425 430

Glu Gly Gly Cys Glu Leu Gly Gly Gly Arg Val Lys Phe Ser Arg Ser
435 440 445

Ala Asp Ala Pro Ala Tyr Gln Gln Gly Gln Asn Gln Leu Tyr Asn Glu
450 455 460

Leu Asn Leu Gly Arg Arg Glu Glu Tyr Asp Val Leu Asp Lys Arg Arg
465 470 475 480

Gly Arg Asp Pro Glu Met Gly Gly Lys Pro Arg Arg Lys Asn Pro Gln
485 490 495

Glu Gly Leu Tyr Asn Glu Leu Gln Lys Asp Lys Met Ala Glu Ala Tyr
500 505 510

Ser Glu Ile Gly Met Lys Gly Glu Arg Arg Arg Gly Lys Gly His Asp
515 520 525

Gly Leu Tyr Gln Gly Leu Ser Thr Ala Thr Lys Asp Thr Tyr Asp Ala
530 535 540

Leu His Met Gln Ala Leu Pro Pro Arg
545 550

<210> SEQ ID NO 41

<211> LENGTH: 248
<212> TYPE: PRT
<213> ORGANISM: Artificial
<220> FEATURE:
<223> OTHER INFORMATION: tTA

<400> SEQUENCE: 41

Met Ser Arg Leu Asp Lys Ser Lys Val Ile Asn Ser Ala Leu Glu Leu
1 5 10 15

Leu Asn Glu Val Gly Ile Glu Gly Leu Thr Thr Arg Lys Leu Ala Gln
20 25 30

Lys Leu Gly Val Glu Gln Pro Thr Leu Tyr Trp His Val Lys Asn Lys
35 40 45

Arg Ala Leu Leu Asp Ala Leu Ala Ile Glu Met Leu Asp Arg His His
50 55 60

Thr His Phe Cys Pro Leu Glu Gly Glu Ser Trp Gln Asp Phe Leu Arg
65 70 75 80

Asn Asn Ala Lys Ser Phe Arg Cys Ala Leu Leu Ser His Arg Asp Gly
85 90 95

Ala Lys Val His Leu Gly Thr Arg Pro Thr Glu Lys Gln Tyr Glu Thr
100 105 110

Leu Glu Asn Gln Leu Ala Phe Leu Cys Gln Gln Gly Phe Ser Leu Glu
115 120 125

Asn Ala Leu Tyr Ala Leu Ser Ala Val Gly His Phe Thr Leu Gly Cys
130 135 140

Val Leu Glu Asp Gln Glu His Gln Val Ala Lys Glu Glu Arg Glu Thr
145 150 155 160

Pro Thr Thr Asp Ser Met Pro Pro Leu Leu Arg Gln Ala Ile Glu Leu
165 170 175

Phe Asp His Gln Gly Ala Glu Pro Ala Phe Leu Phe Gly Leu Glu Leu
180 185 190

Ile Ile Cys Gly Leu Glu Lys Gln Leu Lys Cys Glu Ser Gly Gly Pro
195 200 205

Ala Asp Ala Leu Asp Asp Phe Asp Leu Asp Met Leu Pro Ala Asp Ala
210 215 220

Leu Asp Asp Phe Asp Leu Asp Met Leu Pro Ala Asp Ala Leu Asp Asp
225 230 235 240

Leu Asp Leu Asp Met Leu Pro Gly
245

<210> SEQ ID NO 42
<211> LENGTH: 595
<212> TYPE: PRT
<213> ORGANISM: Artificial
<220> FEATURE:
<223> OTHER INFORMATION: tTa-T2A-CD19t

<400> SEQUENCE: 42

Met Ser Arg Leu Asp Lys Ser Lys Val Ile Asn Ser Ala Leu Glu Leu
1 5 10 15

Leu Asn Glu Val Gly Ile Glu Gly Leu Thr Thr Arg Lys Leu Ala Gln
20 25 30

Lys Leu Gly Val Glu Gln Pro Thr Leu Tyr Trp His Val Lys Asn Lys
35 40 45

Arg Ala Leu Leu Asp Ala Leu Ala Ile Glu Met Leu Asp Arg His His
50 55 60

Thr His Phe Cys Pro Leu Glu Gly Glu Ser Trp Gln Asp Phe Leu Arg

-continued

```
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Ala Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Leu Asp Leu Asp Met Leu Pro Gly Leu Glu Gly Gly Gly Glu Gly Arg
                245                 250                 255

Gly Ser Leu Leu Thr Cys Gly Asp Val Glu Glu Asn Pro Gly Pro Arg
            260                 265                 270

Met Pro Pro Pro Arg Leu Leu Phe Phe Leu Leu Phe Leu Thr Pro Met
        275                 280                 285

Glu Val Arg Pro Glu Glu Pro Leu Val Val Lys Val Glu Glu Gly Asp
    290                 295                 300

Asn Ala Val Leu Gln Cys Leu Lys Gly Thr Ser Asp Gly Pro Thr Gln
305                 310                 315                 320

Gln Leu Thr Trp Ser Arg Glu Ser Pro Leu Lys Pro Phe Leu Lys Leu
                325                 330                 335

Ser Leu Gly Leu Pro Gly Leu Gly Ile His Met Arg Pro Leu Ala Ile
            340                 345                 350

Trp Leu Phe Ile Phe Asn Val Ser Gln Gln Met Gly Gly Phe Tyr Leu
        355                 360                 365

Cys Gln Pro Gly Pro Pro Ser Glu Lys Ala Trp Gln Pro Gly Trp Thr
    370                 375                 380

Val Asn Val Glu Gly Ser Gly Glu Leu Phe Arg Trp Asn Val Ser Asp
385                 390                 395                 400

Leu Gly Gly Leu Gly Cys Gly Leu Lys Asn Arg Ser Ser Glu Gly Pro
                405                 410                 415

Ser Ser Pro Ser Gly Lys Leu Met Ser Pro Lys Leu Tyr Val Trp Ala
            420                 425                 430

Lys Asp Arg Pro Glu Ile Trp Glu Gly Glu Pro Pro Cys Val Pro Pro
        435                 440                 445

Arg Asp Ser Leu Asn Gln Ser Leu Ser Gln Asp Leu Thr Met Ala Pro
    450                 455                 460

Gly Ser Thr Leu Trp Leu Ser Cys Gly Val Pro Pro Asp Ser Val Ser
465                 470                 475                 480

Arg Gly Pro Leu Ser Trp Thr His Val His Pro Lys Gly Pro Lys Ser
                485                 490                 495
```

```
Leu Leu Ser Leu Glu Leu Lys Asp Asp Arg Pro Ala Arg Asp Met Trp
            500                 505                 510

Val Met Glu Thr Gly Leu Leu Leu Pro Arg Ala Thr Ala Gln Asp Ala
        515                 520                 525

Gly Lys Tyr Tyr Cys His Arg Gly Asn Leu Thr Met Ser Phe His Leu
    530                 535                 540

Glu Ile Thr Ala Arg Pro Val Leu Trp His Trp Leu Leu Arg Thr Gly
545                 550                 555                 560

Gly Trp Lys Val Ser Ala Val Thr Leu Ala Tyr Leu Ile Phe Cys Leu
                565                 570                 575

Cys Ser Leu Val Gly Ile Leu His Leu Gln Arg Ala Leu Val Leu Arg
            580                 585                 590

Arg Lys Arg
        595


<210> SEQ ID NO 43
<211> LENGTH: 245
<212> TYPE: PRT
<213> ORGANISM: Artificial
<220> FEATURE:
<223> OTHER INFORMATION: huCCR4 scFv

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser Ser Gly Gly Gly Ser Gly Gly Gly Ser
        115                 120                 125

Gly Gly Gly Gly Ser Asp Ile Val Met Thr Gln Ser Pro Asp Ser Leu
    130                 135                 140

Ala Val Ser Leu Gly Glu Arg Ala Thr Ile Asn Cys Lys Ser Ser Gln
145                 150                 155                 160

Ser Ile Leu Tyr Ser Ser Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys His Gln Tyr Leu Ser Ser Tyr Thr Phe Gly Gln Gly Thr
225                 230                 235                 240

Lys Leu Glu Ile Lys
                245
```

<210> SEQ ID NO 44
<211> LENGTH: 236
<212> TYPE: PRT
<213> ORGANISM: Artificial
<220> FEATURE:
<223> OTHER INFORMATION: huCCR4 scFv

<400> SEQUENCE: 44

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Tyr
20 25 30

Tyr Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Ser Thr Tyr Tyr Arg Pro Leu Asp Tyr Trp Gly Gln Gly Thr
100 105 110

Leu Val Thr Val Ser Ser Ser Gly Gly Gly Gly Ser Asp Ile Val Met
115 120 125

Thr Gln Ser Pro Asp Ser Leu Ala Val Ser Leu Gly Glu Arg Ala Thr
130 135 140

Ile Asn Cys Lys Ser Ser Gln Ser Ile Leu Tyr Ser Ser Asn Gln Lys
145 150 155 160

Asn Tyr Leu Ala Trp Tyr Gln Gln Lys Pro Gly Gln Ser Pro Lys Leu
165 170 175

Leu Ile Tyr Trp Ala Ser Thr Arg Glu Ser Gly Val Pro Asp Arg Phe
180 185 190

Ser Gly Ser Gly Ser Gly Thr Asp Phe Thr Leu Thr Ile Ser Ser Leu
195 200 205

Gln Ala Glu Asp Val Ala Val Tyr Tyr Cys His Gln Tyr Leu Ser Ser
210 215 220

Tyr Thr Phe Gly Gln Gly Thr Lys Leu Glu Ile Lys
225 230 235

<210> SEQ ID NO 45
<211> LENGTH: 240
<212> TYPE: PRT
<213> ORGANISM: Artificial
<220> FEATURE:
<223> OTHER INFORMATION: huCCR4 scFv

<400> SEQUENCE: 45

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ala Ser Tyr
20 25 30

Tyr Met His Trp Met Arg Gln Ala Pro Gly Gln Gly Leu Glu Trp Ile
35 40 45

Gly Trp Ile Asn Pro Gly Asn Val Asn Thr Lys Tyr Asn Glu Lys Phe
50 55 60

Lys Gly Arg Ala Thr Leu Thr Val Asp Thr Ser Thr Asn Thr Ala Tyr

```
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser Gly Gly Gly Gly Ser Gly Gly Gly Gly Ser
        115                 120                 125

Asp Ile Val Met Thr Gln Ser Pro Asp Ser Leu Ala Val Ser Leu Gly
    130                 135                 140

Glu Arg Ala Thr Ile Asn Cys Lys Ser Ser Gln Ser Ile Leu Tyr Ser
145                 150                 155                 160

Ser Asn Gln Lys Asn Tyr Leu Ala Trp Tyr Gln Gln Lys Pro Gly Gln
                165                 170                 175

Ser Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys His Gln
    210                 215                 220

Tyr Leu Ser Ser Tyr Thr Phe Gly Gln Gly Thr Lys Leu Glu Ile Lys
225                 230                 235                 240


<210> SEQ ID NO 46
<211> LENGTH: 4
<212> TYPE: PRT
<213> ORGANISM: Artificial
<220> FEATURE:
<223> OTHER INFORMATION: Linker

<400> SEQUENCE: 46

Gly Gly Gly Ser
1


<210> SEQ ID NO 47
<211> LENGTH: 5
<212> TYPE: PRT
<213> ORGANISM: Artificial
<220> FEATURE:
<223> OTHER INFORMATION: Linker

<400> SEQUENCE: 47

Gly Gly Gly Gly Ser
1               5


<210> SEQ ID NO 48
<211> LENGTH: 22
<212> TYPE: PRT
<213> ORGANISM: Artificial
<220> FEATURE:
<223> OTHER INFORMATION: GMCSFRa signal sequence

<400> SEQUENCE: 48

Met Leu Leu Leu Val Thr Ser Leu Leu Leu Cys Glu Leu Pro His Pro
1               5                   10                  15

Ala Phe Leu Leu Ile Pro
            20
```

CCR4 TARGETED CHIMERIC ANTIGEN RECEPTOR MODIFIED T CELLS FOR TREATMENT OF CCR4 POSITIVE MALIGNANCIES

CLAIM OF PRIORITY

This application is a U.S. National Phase Application under 35 U.S.C. § 371 of International Application No. PCT/US2020/034389, filed on May 22, 2020, which claims the benefit of U.S. Provisional Application Ser. No. 62/852,934, filed on May 24, 2019. The entire contents of the foregoing are incorporated herein by reference.

SEQUENCE LISTING

The instant application contains a Sequence Listing, which has been submitted electronically in ASCII format and is hereby incorporated by reference in its entirety. Said ASCII copy, created on Nov. 16, 2021, is named Sequence-Listing.txt and is 72,000 bytes in size.

TECHNICAL FIELD

This disclosure concerns lymphoma-associated C-C chemokine receptor type 4 (CCR4)-specific chimeric antigen receptor (CAR)-engineered T cells, methods of formulating, and methods of use as anti-cancer agents selective against CCR4-positive cells.

BACKGROUND

CCR4 is expressed at high levels on the malignant skin-homing T cells, and its surface expression is closely associated with the enhanced skin-homing characteristics of cutaneous T cell lymphoma (CTCL) cells and unfavorable disease outcomes (Chang D-H, Sui J, Geng S, Muvaffak A, Bai M, Fuhlbrigge R C, et al. Humanization of an anti-CCR4 antibody that kills Cutaneous T-Cell Lymphoma cells and abrogates suppression by T-regulatory cells. Mol. Cancer Ther. 2012; 11:2451-61). A CAR that targets CCR4 using humanized variable heavy and (Vh) and kappa light (Vl) chain moieties can be derived from an anti-CCR4 antibody that is different from mogamulizumab (Perera L P, Zhang M, Nakagawa M, et al. Chimeric antigen receptor modified T cells that target chemokine receptor CCR4 as a therapeutic modality for T cell malignancies. Am. J. Hematol. 2017; 92(9):892-901).

SUMMARY

Described herein are methods for using CCR4 targeted CAR T cells (also herein called CCR4 CART cells) to treat a variety of cancers, for example, cutaneous T cell lymphoma (CTCL). In addition methods of use as anti-cancer agents selective against CCR4-positive cells, also described herein are methods of decreasing the population of regulatory T cells (Tregs). Without being bound by theory, Tregs can interfere with the desired immune response and methods described here can be used to eliminate or reduce the number of CCR4-positive Tregs.

Described herein is a nucleic acid molecule comprising a nucleotide sequence encoding a chimeric antigen receptor (CAR) or polypeptide, wherein the chimeric antigen receptor or polypeptide comprises: an scFv targeting CCR4, a spacer, a transmembrane domain, a 41-BB co-stimulatory domain, and a CD3 ζ signaling domain.

In various embodiments: the transmembrane domain is selected from: a CD4 transmembrane domain or variant thereof having 1-5 amino acid modifications, a CD8 transmembrane domain or variant thereof having 1-5 amino acid modifications, a CD28 transmembrane domain or a variant thereof having 1-5 amino acid modifications; the spacer comprises 20-150 amino acids and is located between the scFv and the transmembrane domain; the transmembrane domain is a CD4 transmembrane domain or variant thereof having 1-5 amino acid modifications; the transmembrane domain is a CD4 transmembrane domain; the chimeric antigen receptor comprises a transmembrane domain selected from: a CD4 transmembrane domain or variant thereof having 1-2 amino acid modifications, a CD8 transmembrane domain or variant thereof having 1-2 amino acid modifications, a CD28 transmembrane domain or a variant thereof having 1-2 amino acid modifications; the spacer region comprises an amino acid sequence selected from the group consisting of SEQ ID NOs: 2-12 or a variant thereof having 1-5 amino acid modifications; the spacer comprises an IgG hinge region; the spacer comprises 10-50 amino acids; the 4-1BB costimulatory domain comprises the amino acid sequence of SEQ ID NO: 24 or a variant thereof having 1-5 amino acid modifications; the CD3ζ signaling domain comprises the amino acid sequence of SEQ ID NO:21; a linker of 3 to 15 amino acids is located between the 4-1BB costimulatory domain and the CD3 ζ signaling domain or variant thereof; the CAR or polypeptide comprises the amino acid sequence of SEQ ID NO: 29 or a variant thereof having 1-5 amino acid modifications; the scFv comprises the amino acid sequence of SEQ ID NO:1; the nucleic acid molecule of claim 1.

Also disclosed herein is: a viral vector comprising a nucleic acid molecule described herein; a population of human T cells (e.g., a population comprising central memory T cells) transduced by a vector comprising a nucleic acid molecule described herein. In some embodiments, the vector is an expression vector in which expression of the CCR4 CAR or CCR4 polypeptide is under the control of an inducible promoter. In some embodiments, the expression of the CCR4 CAR or CCR4 polypeptide is under the control of a Tet Off system.

Also described herein is a method of treating CCR4 positive cancers (including, e.g., peripheral T cell lymphoma, adult T cell lymphoma, anaplastic large cell lymphoma, primary cutaneous T cell lymphoma, renal cell carcinoma, lung cancer, hepatocellular carcinoma, and diffuse large B-cell lymphoma) in a patient comprising administering a population of autologous or allogeneic human T cells transduced by a vector comprising a nucleic acid molecule described herein, wherein the T cell lymphoma comprises cells expressing CCR4. In various embodiments: the chimeric antigen receptor or polypeptide is administered locally or systemically; the CCR4-expressing cells are cancerous T cells; and the chimeric antigen receptor or polypeptide is administered by single or repeat dosing.

In various embodiments: the chimeric antigen receptor or polypeptide comprises: a huCCR4 scFv (e.g., an scFv comprising the amino acid sequence (SEQ ID NO: 1)

QVQLVQSGAEVVKPGASVKISCKASGYTFTDHAIHWVKQNPGQRLEWIGY

FSPGNDDFKYNERFKGKATLTADTSASTAYVELSSLRSEDTAVYFCTRSL

NMAYWGQGTLVTVSSGSTSGGGSGGGSGGGGSSDIVMSQSPDSLAVSLGE

-continued

```
RVTLNCKSSQSLLYSGNQKNYLAWYQQKPGQSPKLLIYWASARESGVPDR

FSGSGSGTDFTLTISSVQAEDVAVYYCQQYYSYPLTFGAGTKLELK.
with up to 10 single amino acid substitutions)
```

In various embodiments: the chimeric antigen receptor or polypeptide comprises: a huCCR4 scFv (e.g., an scFv comprising the amino acid sequence

```
                                          (SEQ ID NO: 43)
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGE

RATINCKSSQSILYSSNQKNYLAWYQQKPGQSPKLLIYWASTRESGVPDR

FSGSGSGTDFTLTISSLQAEDVAVYYCHQYLSSYTFGQGTKLEIK.
with up to 10 single amino acid substitutions)
```

In various embodiments: the chimeric antigen receptor or polypeptide comprises: a huCCR4 scFv (e.g., an scFv comprising the amino acid sequence

```
                                          (SEQ ID NO: 44)
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSSSGGGGSDIVMTQSPDSLAVSLGERATINCKSS

QSILYSSNQKNYLAWYQQKPGQSPKLLIYWASTRESGVPDRFSGSGSGTD

FTLTISSLQAEDVAVYYCHQYLSSYTFGQGTKLEIK.
with up to 10 single amino acid substitutions)
```

In various embodiments: the chimeric antigen receptor or polypeptide comprises: a huCCR4 scFv (e.g., an scFv comprising the amino acid sequence

```
                                          (SEQ ID NO: 45)
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSSGGGGSGGGGSDIVMTQSPDSLAVSLGERATIN

CKSSQSILYSSNQKNYLAWYQQKPGQSPKLLIYWASTRESGVPDRFSGSG

SGTDFTLTISSLQAEDVAVYYCHQYLSSYTFGQGTKLEIK.
with up to 10 single amino acid substitutions)
```

Also described a T cells harboring a vector expressing the CAR or polypeptide. In various embodiments: at least 20%, 30%, or 40% of the transduced human T cells are central memory T cells; at least 30% of the transduced human T cells are CD4+ and CD62L+ or CD8+ and CD62L+; the population of human T cells are autologous to the patient; and the population of human T cells are allogenic to the patient.

CCR4 Targeted CAR

The CCR4 targeted CAR or CCR4 targeted polypeptide described herein include a CCR4 targeting scFv. In some embodiments, an scFv comprising the amino acid sequence:

```
                                          (SEQ ID NO: 43)
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSSSGGGSGGGGSGGGGSDIVMTQSPDSLAVSLGE

RATINCKSSQSILYSSNQKNYLAWYQQKPGQSPKLLIYWASTRESGVPDR

FSGSGSGTDFTLTISSLQAEDVAVYYCHQYLSSYTFGQGTKLEIK
or comprising the sequence
                                          (SEQ ID NO: 32)
QVQLVQSGAEVKKPGASVKVSCKASGYTFASYYMHWMRQAPGQGLEWIGW

INPGNVNTKYNEKFKGRATLTVDTSTNTAYMELSSLRSEDTAVYYCARST

YYRPLDYWGQGTLVTVSS
and the sequence
                                          (SEQ ID NO: 33)
DIVMTQSPDSLAVSLGERATMSCKSSQSILYSSNQKNYLAWYQQKPGQSP

KLLIYWASTRESGVPDRFSGSGSGTDFTLTISSLQAEDVAVYYCHQYLSS

YTFGQGTKLEIK.
joined by a flexible linker
```

In some embodiments, an scFv comprises the amino acid sequence:

```
                                          (SEQ ID NO: 34)
QVQLVQSGAEVKKPGASVKVSCKASGYTFASQWMHWMRQAPGQGLEWIGW

INPGNVNTKYNEKFKGRATLTVDTSTNTAYMELSSLRSEDTAVYYCARST

WYRPLDYWGQGTLVTVSS
and the sequence
                                          (SEQ ID NO: 35)
DIVMTQSPDSLAVSLGERATMSCKSSQSILYSSNQKNYLAWYQQKPGQSP

KLLWWASTRESGVPDRFSGSGSGTDFTLTISSLQAEDVAVYYCHQYISSY

TFGQGTKLEIK.
joined by a flexible linker
```

In some embodiments, an scFv comprises the amino acid sequence:

```
                                          (SEQ ID NO: 36)
QVQLVQSGAEVKKPGASVKVSCKASGYTFASAWMHWMRQAPGQGLEWIGW

INPGNVNTKYNEKFKGRATLTVDTSTNTAYMELSSLRSEDTAVYYCARST

YYRPLDYWGQGTLVTVSS
and the sequence
                                          (SEQ ID NO: 37)
DIVMTQSPDSLAVSLGERATMSCKSSQSILYSSNQKNYLAWYQQKPGQSP

KLLWWASTRESGVPDRFSGSGSGTDFTLTISSLQAEDVAVYYCHQYMSSY

TFGQGTKLEIK.
joined by a flexible linker
```

In some embodiments, a useful flexible linker is 1, 2, 3, 4, 5, 6, 7, 8, 9, or 10 repeats of the sequence GGGS (SEQ ID NO:46). In some embodiments, a useful flexible linker is 1, 2, 3, 4, 5, 6, 7, 8, 9, or 10 repeats of the sequence GGGGS (SEQ ID NO:47).

A useful CCR4 CAR or CCR4 polypeptide can consist of or comprises the amino acid sequence of SEQ ID NO:38, 39, or 40 (mature CAR lacking a signal sequence) or the CCR4 CAR or CCR4 polypeptide can consist of or comprise the amino acid sequence of SEQ ID NO:29, 30, or 31 (immature CAR having a GMCSFRa signal sequence). The CAR or polypeptide can be expressed in a form that includes a signal sequence, e.g., a human GM-CSF receptor alpha signal sequence (MLLLVTSLLLCELPHPAFLLIP; SEQ ID NO:43). The CAR or polypeptide can be expressed with additional sequences that are useful for monitoring expression, for example, a T2A skip sequence and a truncated EGFRt or truncated CD19. Thus, the CAR or polypeptide can comprise or consist of the amino acid sequence of SEQ ID Nos: 1, 29, 30, 31, 38, 39, 40, 43, 44, or 45 or can comprise or consist of an amino acid sequence that is at least 95%, 96%, 97%, 98% or 99% identical to SEQ ID Nos: 1, 29, 30, 31, 38, 39, 40, 43, 44, or 45. The CAR or polypeptide can comprise or consist of the amino acid sequence of any of SEQ ID Nos 1, 29, 30, 31, 38, 39, 40, 43, 44, or 45 with up to 1, 2, 3, 4 or 5 amino acid changes (preferably conservative amino acid changes) and SEQ ID NO:37 with up to 1, 2, 3, 4 or 5 amino acid changes (preferably conservative amino acid changes) joined by a flexible linker.

In some embodiments, the nucleic acid encoding amino acid sequences SEQ ID NOs:1, 29-40, and 43-45 are codon optimized.

Spacer Region

The CAR or polypeptide described herein can include a spacer located between the CCR4 targeting domain (i.e., a CCR4 targeted ScFv or variant thereof) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (5228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHLCPSPLFPGPSKP (SEQ ID NO: 6) |
| CD8 hinge-48aa | 48 aa | AKPTTTPAPRPPTPAPTIASQPLSLRPEACRPAAGGAVHTRGLDFACD (SEQ ID NO: 7) |
| CD8 hinge-45aa | 45 aa | TTTPAPRPPTPAPTIASQPLSLRPEACRPAAGGAVHTRGLDFACD (SEQ ID NO: 8) |
| IgG4(HL-CH3) Also called IgG4(HL-ΔCH2) (includes 5228P in hinge) | 129 aa | ESKYGPPCPPCPGGGSSGGGSGGQPREPQVYTLPPSQEEMTKNQVSLTCL VKGFYPSDIAVEWESNGQPENNYKTTPPVLDSDGSFFLYSRLTVDKSRWQE GNVFSCSVMHEALHNHYTQKSLSLSLGK (SEQ ID NO: 9) |
| IgG4(L235E, N297Q) | 229 aa | ESKYGPPCPSCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 10) |
| IgG4(5228P, L235E, N297Q) | 229 aa | ESKYGPPCPPCPAPEFEGGPSVFLFPPKPKDTLMISRTPEVTCVVVDVSQED PEVQFNWYVDGVEVHQAKTKPREEQFQSTYRVVSVLTVLHQDWLNGKEY KCKVSNKGLPSSIEKTISKAKGQPREPQVYTLPPSQEEMTKNQVSLTCLVKG FYPSDIAVEWESNGQPENNYKTTPPVLDSDGSFFLYSRLTVDKSRWQEGN VFSCSVMHEALHNHYTQKSLSLSLGK (SEQ ID NO: 11) |
| IgG4(CH3) Also called IgG4(ΔCH2) | 107 aa | GQPREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQKSL SLSLGK (SEQ ID NO: 12) |

conservative amino acid changes). The CAR or polypeptide can comprise SEQ ID NO:32 with up to 1, 2, 3, 4 or 5 amino acid changes (preferably conservative amino acid changes) and SEQ ID NO:33 with up to 1, 2, 3, 4 or 5 amino acid changes (preferably conservative amino acid changes) joined by a flexible linker. The CAR or polypeptide can comprise SEQ ID NO:34 with up to 1, 2, 3, 4 or 5 amino acid changes (preferably conservative amino acid changes) and SEQ ID NO:35 with up to 1, 2, 3, 4 or 5 amino acid changes (preferably conservative amino acid changes) joined by a flexible linker. The CAR or polypeptide can comprise SEQ ID NO:36 with up to 1, 2, 3, 4 or 5 amino acid changes Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain (called CH3 or ΔCH2) or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3). The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLTCLVKGFYPSDIAVEWESNGQPENNYKTTPPV LDSDGSFFLYSRLTVDKSRWQEGNVFSCSVMH EALHNHYTQKSLSLSLGK (SEQ ID NO:12). Thus, the entire linker/spacer region can comprise the sequence: ESKYGPPCPPCPGGGSSGGGSGGQPREPQVYTLPPSQEEMTKNQVSLTCLVKGFYPS DIAVEWESNGQPENNYKTTPPVLDSDGSFFLYSRLTVDKSRWQEGNVFSCS VMHEA LHNHYTQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the. Table 2 includes examples of suitable transmembrane domains. Where a spacer region is present, the transmembrane domain (TM) is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTALFL (SEQ ID NO: 13) |
| CD28 | NM_006139 | 27 aa | FWVLVVVGGVLACYSLLVTVAFIIFWV (SEQ ID NO: 14) |
| CD28(M) | NM_006139 | 28 aa | MFWVLVVVGGVLACYSLLVTVAFIIFWV (SEQ ID NO: 15) |
| CD4 | M35160 | 22 aa | MALIVLGGVAGLLLFIGLGIFF (SEQ ID NO: 16) |
| CD8tm | NM_001768 | 21 aa | IYIWAPLAGTCGVLLLSLVIT (SEQ ID NO: 17) |
| CD8tm2 | NM_001768 | 23 aa | IYIWAPLAGTCGVLLLSLVITLY (SEQ ID NO: 18) |
| CD8tm3 | NM_001768 | 24 aa | IYIWAPLAGTCGVLLLSLVITLYC (SEQ ID NO: 19) |
| 41BB | NM_001561 | 27 aa | IISFFLALTSTALLFLLFF LTLRFSVV (SEQ ID NO: 20) |

Costimulatory Domain

The costimulatory domain can be any domain that is suitable for use with a CD3ζ signaling domain. In some cases the co-signaling domain is a 4-1BB co-signaling domain that includes a sequence that is at least 90%, at least 95%, at least 98% identical to or identical to: KRGRKKLLYIFKQPFMRPVQTTQEEDGCSCRFPEEEEGGCEL (SEQ ID NO:24). In some cases, the 4-1BB co-signaling domain has 1, 2, 3, 4 of 5 amino acid changes (preferably conservative) compared to SEQ ID NO:24.

The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLYNELNLGRREEYDVLDKRRGR DPEMGGKPRRKNPQEGLYNELQKDKMAEAYSEIGMKGERR RGKGHDGLYQGLSTATKDTYDALHMQALPPR (SEQ ID NO: 21) |
| CD28 | NM_006139 | 42 aa | RSKRSRLLHSDYMNMTPRRPGPTRKHYQPYAPPRDFAAYRS (SEQ ID NO: 22) |
| CD28gg* | NM_006139 | 42 aa | RSKRSRGGHSDYMNMTPRRPGPTRKHYQPYAPPRDFAAYR S (SEQ ID NO: 23) |
| 41BB | NM_001561 | 42 aa | KRGRKKLLYIFKQPFMRPVQTTQEEDGCSCRFPEEEEGGCEL (SEQ ID NO: 24) |
| OX40 | | 42 aa | ALYLLRRDQRLPPDAHKPPGGGSFRTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and a short linker consisting of 2-10, e.g., 3 amino acids (e.g., GGG) is can be positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to: RVKFSRSADAPAYQQGQNQLYNELNLGR-REEYDVLDKRRGRDPEMGGKPRRKNPQ EGLY-NELQKDKMAEAYSEIGMKGERRRGKGHDGLYQGL-STATKDTYDALHMQAL PPR (SEQ ID NO:21). In some cases, the CD3ζ signaling has 1, 2, 3, 4 of 5 amino acid changes (preferably conservative) compared to SEQ ID NO:21.

Truncated EGFR or CD19

The CD3ζ signaling domain can be followed by a ribosomal skip sequence (e.g., LEGGGEGRGSLLTCGD-VEENPGPR; SEQ ID NO:27) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDL-HILPVA FRGDSFTHTPPLDPQELDI-LKTVKEITGFLLIQAWPENRTDLHAFENLEIIRGRTKQ HG QFSLAVVSLNITSLGLRSLKEISDGDVIISGNKNL-CYANTINWKKLFGTSGQKTKIISN RGENSCK-ATGQVCHALCSPEGCWGPEPRDCVSCRNVSR-GRECVDKCNLLEGEPREF VENSECIQCHPECLPQAMNITCTGRGPDNCI-QCAHYIDGPHCVKTCPAGVMGENNTL VWKY-ADAGHVCHLCHPNCTYGCTGPGLEGCPTNGPKIPSI-ATGMVGALLLLLVVAL GIGLFM (SEQ ID NO:28). In some cases, the truncated EGFR has 1, 2, 3, 4 of 5 amino acid changes (preferably conservative) compared to SEQ ID NO:28. Alternatively the CD3ζ signaling domain can be followed by a ribosomal skip sequence (e.g., LEGGGEGRGSLLTCGDVEENPGPR; SEQ ID NO:27) and a truncated CD19R (also called CD19t) having a sequence that is at least 90%, at least 95%, at least 98% identical to or identical to:

(SEQ ID NO: 26)
MPPPRLLFFLLFLTPMEVRPEEPLVVKVEEGDNAVLQCLKGTSDGPTQQL

TWSRESPLKPFLKLSLGLPGLGIHMRPLAIWLFIFNVSQQMGGFYLCQPG

-continued
PPSEKAWQPGWTVNVEGSGELFRWNVSDLGGLGCGLKNRSSEGPSSPSGK

LMSPKLYVWAKDRPEIWEGEPPCVPPRDSLNQSLSQDLTMAPGSTLWLSC

GVPPDSVSRGPLSWTHVHPKGPKSLLSLELKDDRPARDMWVMETGLLLPR

ATAQDAGKYYCHRGNLTMSFHLEITARPVLWHWLLRTGGWKVSAVTLAYL

IFCLCSLVGILHLQRALVLRRKR

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In some cases, the CCR4 CAR or CCR4 polypeptide can be produced using a vector in which the CAR open reading frame is followed by a T2A ribosome skip sequence and a truncated EGFR (EGFRt), which lacks the cytoplasmic signaling tail. In this arrangement, co-expression of EGFRt provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt incorporated in the CCR4 CAR lentiviral vector can act as suicide gene to ablate the CAR+ T cells in cases of treatment-related toxicity.

The CAR or polypeptide described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte, and most preferably an autologous T lymphocyte.

Various T cell subsets isolated from the patient can be transduced with a vector for CAR or polypeptide expression. Central memory T cells are one useful T cell subset. Central memory T cell can be isolated from peripheral blood mononuclear cells (PBMC) by selecting for CD45RO+/CD62L+ cells, using, for example, the CliniMACS® device to immunomagnetically select cells expressing the desired receptors. The cells enriched for central memory T cells can be activated with anti-CD3/CD28, transduced with, for example, a lentiviral vector that directs the expression of an CCR4 CAR as well as a non-immunogenic surface marker for in vivo detection, ablation, and potential ex vivo selection. The activated/genetically modified CCR4 central memory T cells can be expanded in vitro with IL-2/IL-15 and then cryopreserved. Additional methods of preparing CART cells can be found in PCT/US2016/043392.

Methods for preparing useful T cell populations are described in, for example, WO 2017/015490 and WO 2018/102761. In some cases, it may be useful to use natural killer (NK) cells, e.g., allogenic NK cells derived from peripheral blood or cord blood. In other cases, NK cells can be derived from human embryonic stem cells (hESCs) or induced pluripotent stem cells (iPSCs).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety for any and all purposes. In case of conflict, the present specification, including definitions, will control.

Other features and advantages of the invention will be apparent from the following detailed description and figures, and from the claims.

DESCRIPTION OF DRAWINGS

FIG. 1 shows a schematic depicting three CCR4 CAR constructs differing in the spacer region.

FIG. 10A-10C show the annotated amino acid sequences of CAR1 (CCR4 L CAR) (A; SEQ ID NO: 29) CAR2 (CCR4 EQ CAR) (B; SEQ ID NO: 30), and CAR3 (CCR4 ΔCH2 CAR; also called CCR4 CH3 CAR) (C; SEQ ID NO: 31).

FIGS. 13A-13E show inducible CAR constructs. FIG. 13A shows the shorthand of four inducible CCR4 CAR constructs. FIG. 13B shows the plasmid map of inducible CAR1 (CCR4 EQ with CD19t). FIG. 13C shows the plasmid map of inducible CAR2 (CCR4 CH3 with CD19t). FIG. 13D shows the plasmid map of inducible CAR3 (CCR4 EQ). FIG. 13E shows the plasmid map of inducible CAR4 (CCR4 CH3; also called CCR4 ΔCH2).

FIGS. 14A-14C show the annotated amino acid sequences (without the signal sequence) of CAR1 (CCR4 L CAR) (A; SEQ ID NO: 38) CAR2 (CCR4 EQ CAR) (B; SEQ ID NO: 39), and CAR3 (CCR4 ΔCH2 CAR; also called CCR4 CH3 CAR) (C; SEQ ID NO: 40).

FIGS. 15A-15B show the annotated amino acid sequences of tTA (A; SEQ ID NO: 41) and T2A-CD19t (B; SEQ ID NO: 42) as used in the plasmid maps.

DETAILED DESCRIPTION

Figure 2:
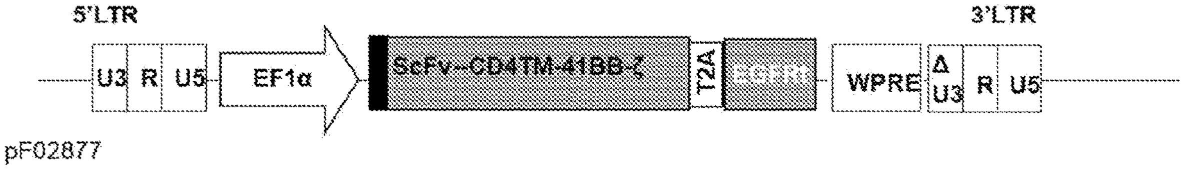
FIG. 2 shows a schematic of CCR4 CAR design: Three different CCR4 CAR constructs were designed. All three of the constructs express the same codon optimized, humanized CCR4 single chain variable fragment. All of the CAR constructs also express a CD4 transmembrane (TM) domain, a 41BB costimulatory domain, a CD3 zeta (ζ) domain, and a separate protein (truncated EGFR) to mark the successful transduction of the cells with the CAR construct. The three CCR4 CAR constructs differ in their spacer domains.
Figure 3A:
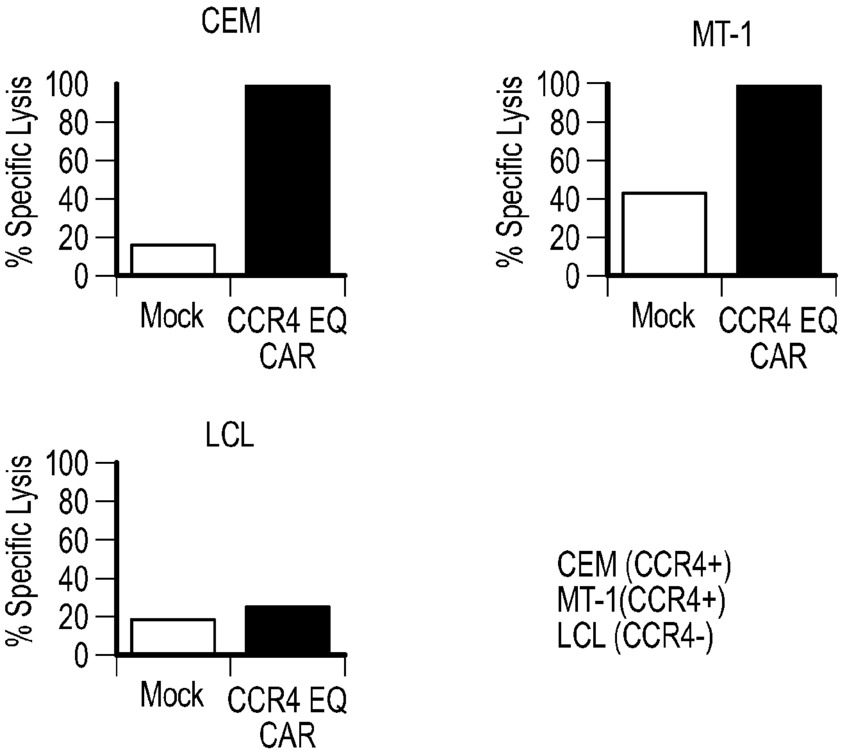
FIGS. 3A-3B shows results from a 48 hr long term killing assay with CCR4 EQ CAR at 1:10 E:T (A) and rechallenge assays (B). In the rechallenge assays, after 2 days at an E:T of 1:2 tumor cells were added back so that the 1:2 E:T is re-established. Lysis was analyzed 48 hrs later.
Figure 3B:
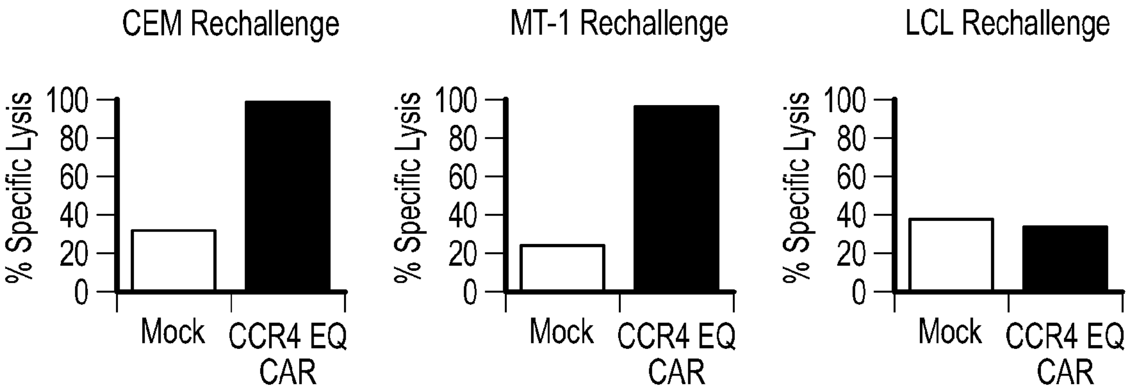

In this disclosure the generation and anti-tumor efficacy of CAR with a humanized anti-human CCR4 scFv antigen-binding domain and a 4-1BB intracellular co-stimulatory signaling domain are described. The CCR4 CAR T cells exhibited potent antigen-dependent cytotoxicity against multiple CCR4-expressing human T cell cancer lines. Intravenous in vivo delivery of CCR4 CAR T cells in human leukemia/lymphoma murine tumor models conferred elimination of antigen-positive disease and extension of overall survival.

The present disclosure also provides methods for treating subjects with a T-cell cancer, including a non-Hodgkin lymphoma, a peripheral T-cell lymphoma (PTCL), an anaplastic large cell lymphoma, a lymphoblastic lymphoma, precursor T-lymphoblastic lymphoma, an angioimmunoblastic T-cell lymphoma, Cutaneous T-Cell Lymphoma (CTCL), mycosis fungoides (MF), Sézary syndrome (SS), and the like. T cell lymphomas encompass a variety of conditions including without limitation: (a) lymphoblastic lymphomas in which the malignancy occurs in primitive lymphoid progenitors from the thymus; (b) mature or peripheral T cell neoplasms, including T cell prolymphocytic leukemia, T-cell granular lymphocytic leukemia, NK-cell leukemia, cutaneous T cell lymphoma (Mycosis fungoides and Sezary syndrome), anaplastic large cell lymphoma, T cell type, enteropathy-type T cell lymphoma, Adult T-cell leukemia/lymphoma including those associated with HTLV-1, and angioimmunoblastic T cell lymphoma, and subcutaneous panniculitic T cell lymphoma; and (c) peripheral T cell lymphomas that initially involve a lymph node paracortex and never grow into a true follicular pattern.

EXAMPLES

The invention is further described in the following examples, which do not limit the scope of the invention described in the claims.

Materials and Methods

The following materials and methods were used in the Examples set forth herein.

Cell Lines

The CEM (adult T cell leukemia line), MT-1 (adult T cell leukemia line), and LCL (generated from PBMC; Engraftment of human central memory-derived effector CD8+ T cells in immunodeficient mice. Xiuli Wang, et al. (2011) Blood) cell lines were cultured in RPMI-1640 (Lonza) containing 10% fetal bovine serum (FBS, Hyclone) (complete RPMI). The 293T cell lines were cultured in Dulbecco's Modified Eagles Medium (DMEM, Life Technologies) containing 10% FBS, 1× AA, 25 mM HEPES (Irvine Scientific), and 2 mM L-Glutamine (Fisher Scientific) (complete DMEM). All cells were cultured at 37° C. with 5% $CO_2$. HUT78 cells were cultured in IMDM (Iscove's Modified Dulbecco's Medium; Fisher Scientific) with 20% FBS.

DNA Constructs and Lentivirus Production

Tumor cells were engineered to express enhanced green fluorescent protein and firefly luciferase (eGFP/ffluc) by transduction with epHIV7 lentivirus carrying the eGFP/ffluc fusion under the control of the EF1α promoter as described previously (Lenalidomide Enhances the Function of CS1 Chimeric Antigen Receptor-Redirected T Cells Against Multiple Myeloma (Wang et al). Clinical Cancer Research 2018). The humanized scFv sequence used in the CAR construct was obtained from a monoclonal antibody clone h1567 that targets CCR4 (Chang D-H, Sui J, Geng S, Muvaffak A, Bai M, Fuhlbrigge R C, et al. Humanization of an anti-CCR4 antibody that kills Cutaneous T-Cell Lymphoma cells and abrogates suppression by T-regulatory cells. Mol. Cancer Ther. 2012; 11:2451-61).

Lentivirus was generated using a modified polyethylenimine (PEI) mediated transfection method (Optimization of lentiviral vector production using polyethylenimine-mediated transfection. Yong Tang, et al. Oncology Letters. 2015). Briefly, 293T cells were transfected with packaging plasmid and CAR lentiviral backbone plasmid using a modified PEI method. Viral supernatants were collected after 3 to 4 days. Supernatants were concentrated via high-speed centrifugation and lentiviral pellets were resuspended in phosphate-buffered saline (PBS)-lactose solution (4 g lactose per 100 mL PBS), aliquoted and stored at −80° C. Lentiviral titers were quantified using jurkat cells based on EGFRt expression.

T Cell Isolation, Lentiviral Transduction, and Ex Vivo Expansion

Leukapheresis products were obtained from consented research participants (healthy donors) under protocols approved by the City of Hope Internal Review Board (IRB). On the day of leukapheresis, peripheral blood mononuclear cells (PBMC) were isolated by density gradient centrifugation over Ficoll-Paque (GE Healthcare) followed by multiple washes in PBS/EDTA (Miltenyi Biotec). Cells were rested overnight at room temperature (RT) on a rotator, and subsequently washed and resuspended in X-VIVO T cell medium (Lonza) containing 10% FBS (complete X-VIVO). Up to $5.0\times10^9$ PBMC were incubated with anti-CD14 and anti-CD25 microbeads (Miltenyi Biotec) for 30 min at RT and magnetically depleted using the CliniMACS® system (Miltenyi Biotec) according to the manufacturer's protocol and these were termed depleted PBMCs (dPBMC). dPBMC were frozen in CryoStor® CS5 (StemCell Technologies) until further processing.

T cell activation and transduction was performed as described previously (Co-stimulatory signaling determines tumor antigen sensitivity and persistence of CAR T cells targeting PSCA+ metastatic prostate cancer. Priceman Saul J, et al. 2018. Oncoimmunology). Briefly, freshly thawed dPBMC were washed once and cultured in complete X-VIVO containing 100 U/mL recombinant human IL-2 (rhlL-2, Novartis Oncology) and 0.5 ng/mL recombinant human IL-15 (rhIL-15, CellGenix). For CAR lentiviral transduction, T cells were cultured with CD3/CD28 Dynabeads® (Life Technologies), protamine sulfate (APP Pharmaceuticals), cytokine mixture (as stated above) and desired lentivirus at a multiplicity or infection (MOI) of 1-3 the day following bead stimulation. Cells were then cultured in and replenished with fresh complete X-VIVO containing cytokines every 2-3 days. After 7 days, beads were magnetically removed, and cells were further expanded in complete X-VIVO containing cytokines to achieve desired cell yield. Following further expansion, cells were frozen in CryoStor® CS5 prior to in vitro functional assays and in vivo tumor models. Purity and phenotype of CAR T cells were verified by flow cytometry.

Flow Cytometry

For flow cytometric analysis, cells were resuspended in FACS buffer (Hank's balanced salt solution without Ca2+, Mg2+, or phenol red (HBSS−/−, Life Technologies) containing 2% FBS and 1× AA). Cells were incubated with primary antibodies for 30 minutes at 4° C. in the dark. For secondary staining, cells were washed twice prior to 30 min incubation at 4° C. in the dark with either Brilliant Violet 510 (BV510), fluorescein isothiocyanate (FITC), phycoerythrin (PE), peridinin chlorophyll protein complex (PerCP), PerCP-Cy5.5, PE-Cy7, allophycocyanin (APC), or APC-Cy7 (or APC-eFluor780)-conjugated antibodies. Antibodies against CD3 (BD Biosciences, Clone: SK7), CD4

(BD Biosciences, Clone: SK3), CD8 (BD Biosciences, Clone: SK1), CD14 (BD Biosciences, Clone: MΦP9), CD19 (BD Biosciences, Clone: SJ25C1), CD25 (BD Biosciences, Clone: 2A3), mouse CD45 (BioLegend, Clone: 30-F11), CD45 (BD Biosciences, Clone: 2D1), CD69 (BD Biosciences, Clone: L78), CD137 (BD Biosciences, Clone: 4B4-1), MUC1 (BioLegend, Clone 16A), biotinylated Protein-L (GenScript USA), CCR4 (Clone, L291H4), and streptavidin (BD Biosciences) were used. Cell viability was determined using 4',6-diamidino-2-phenylindole (DAPI, Sigma). Flow cytometry was performed on a MACSQuant Analyzer 10 (Miltenyi Biotec), and the data was analyzed with FlowJo software (v10, TreeStar).

In Vitro Tumor Killing and Rechallenge Assays

For tumor killing assays, CAR T cells and tumor targets were co-cultured at indicated effector:tumor (E:T) ratios in complete X-VIVO in the absence of exogenous cytokines in 96-well plates for 24 to 72 h and analyzed by flow cytometry as described above. Tumor killing by CAR T cells was calculated by comparing GFP positive tumor cell counts relative to that observed when targets were co-cultured with Mock (untransduced) T cells. For rechallenge assays, 24-72 hours after completion of the killing assay, CART cells and tumor targets were again co-cultured at indicated effector: tumor (E:T) ratios in complete X-VIVO in the absence of exogenous cytokines in 96-well plates for 24 to 72 h and analyzed by flow cytometry as described above.

In Vivo Tumor Studies

All animal experiments were performed under protocols approved by the City of Hope Institutional Animal Care and Use Committee. For in vivo tumor studies, CEM cells ($3.0\times10^6$) were prepared in a final volume of 150 μl HBSS−/− and engrafted in 6 to 8 week old female or male NSG mice by injection. In some embodiments, engraftment comprises subcutaneous (s.c.) injection or intravenous (i.v.) injection. Tumor growth was monitored at least once a week via biophotonic imaging (Xenogen, LagoX) and flux signals were analyzed with Living Image software (Xenogen). For imaging, mice were i.p. injected with 150 μL D-luciferin potassium salt (Perkin Elmer) suspended in PBS at 4.29 mg/mouse. Once flux signals reached desired levels, day 4 or 5, T cells were prepared in 1×PBS, and mice were treated with 150 μL intravenous (i.v.) injection of $3.0\times10^6$ Mock or CCR4 CAR2 T cells. In the CEM tumor model, the impact of treatment with i.v. CCR4 EQ CAR T cells was examined starting at day 4. Humane endpoints were used in determining survival. Mice were euthanized upon signs of distress such as labored or difficulty breathing, apparent weight loss, impaired mobility, or evidence of being moribund. At predetermined time points or at moribund status, mice were euthanized and tissues were harvested and processed for flow cytometry and/or immunohistochemistry as described below.

Peripheral blood was collected from isoflurane-anesthetized mice by retro-orbital (RO) bleed through heparinized capillary tubes (Chase Scientific) into polystyrene tubes containing a heparin/PBS solution (1000 units/mL, Sagent Pharmaceuticals). Volume of each RO blood draw (approximately 120 μL/mouse) was recorded for cell quantification per μL blood. Red blood cells (RBCs) were lysed with 1× Red Cell Lysis Buffer (Sigma) according to the manufacturer's protocol and then washed, stained, and analyzed by flow cytometry as described above.

Example 1: Construction of CCR4 CAR T Cells Containing Differing Linkers

The studies described below show that CCR4 CAR can be stably expressed on primary T cells.

Three CCR4 targeting CAR constructs were designed (FIGS. 1 and 2). All three of the constructs expressed the same codon optimized, humanized CCR4 single chain variable fragment. The CAR constructs also included a CD4 transmembrane domain (TM), a 41BB costimulatory domain, a CD3 zeta domain. The CARs were co-expressed with truncated EGFR, which serve as a marker for the successful transduction of the cells with the CAR construct. The three CCR4 CAR constructs differ in their linker (FIG. 2). Without being bound by theory, differing lengths in the extracellular portion of the construct may provide differences in the CARs ability to bind the antigen and transmit activation signals after antigen binding. These differences could also result differential killing of CCR4 expressing tumor cells (FIG. 1).

Figure 4:
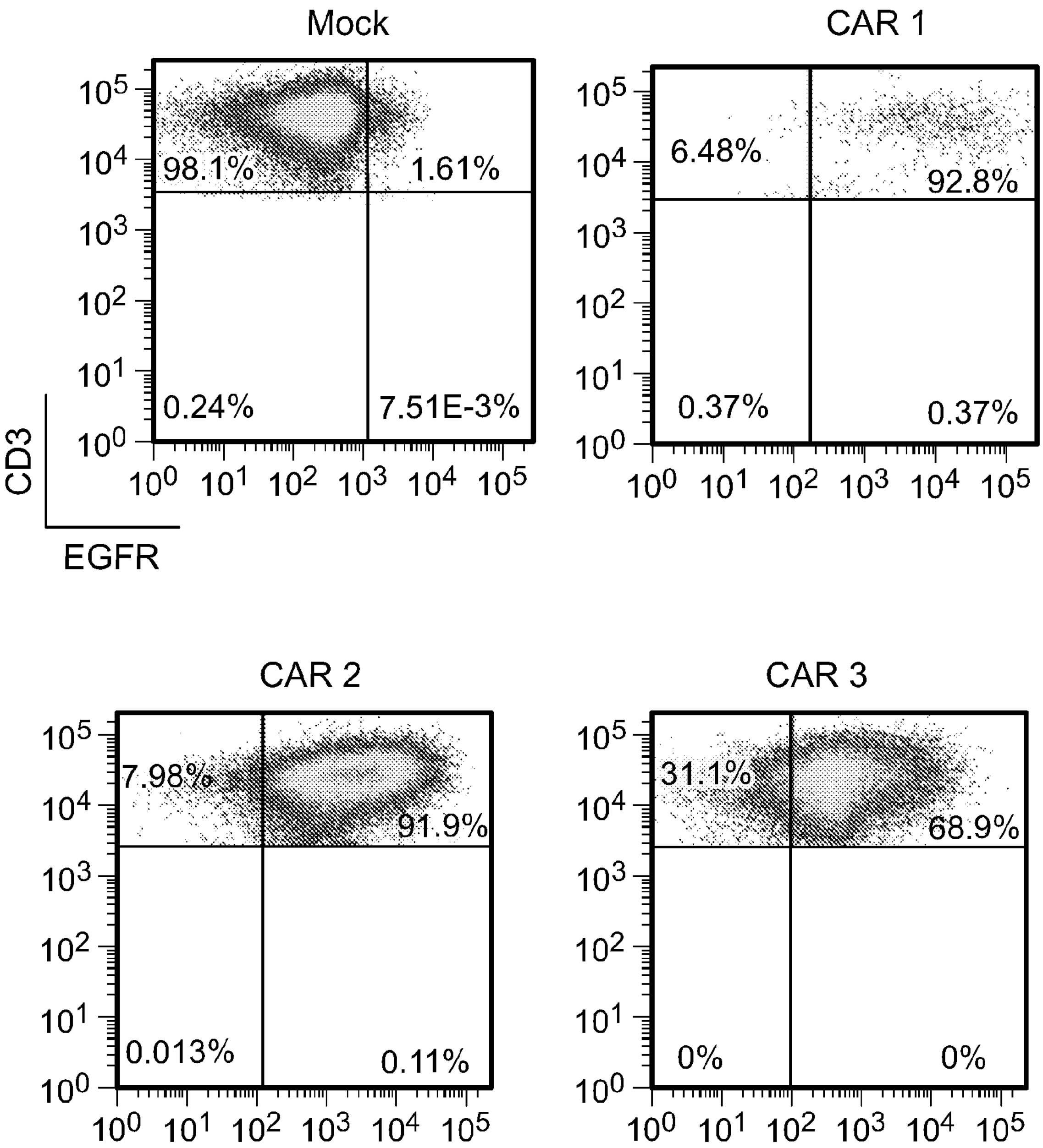
FIG. 4 shows results from experiments with CCR4 CAR T cells where EGFRt is used as a tracking marker and its expression was stable through 7 day culture duration. Mock (untransduced) and CCR4 CAR T cells were evaluated by flow cytometry for EGFR expression to detect transduction of CARs.
Figure 5A:
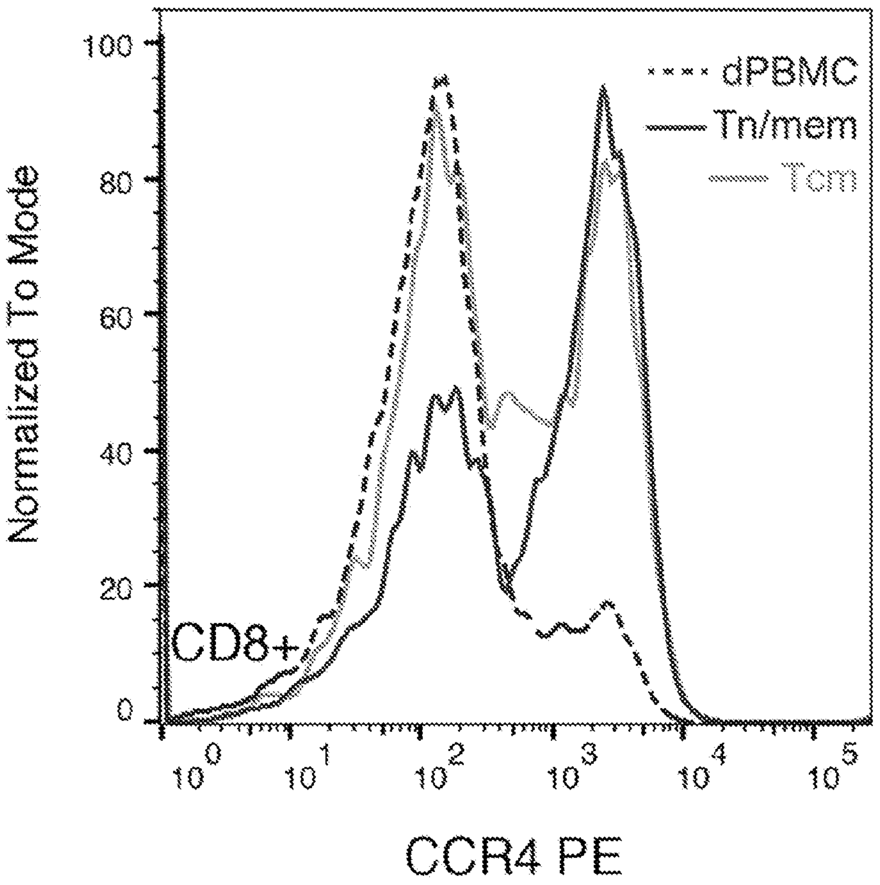
FIGS. 5A-5B show results of flow cytometric analysis of CCR4 expression in different T cell subpopulations. T cell populations of depleted PBMC (CD14−CD25−; also called "dPBCM"), naïve memory T cells (Tn/mem) and central memory T cells (Tcm) were stained for CCR4 expression via flow cytometry in CD8+ (FIG. 5A) and CD4+ (FIG. 5B).
Figure 5B:
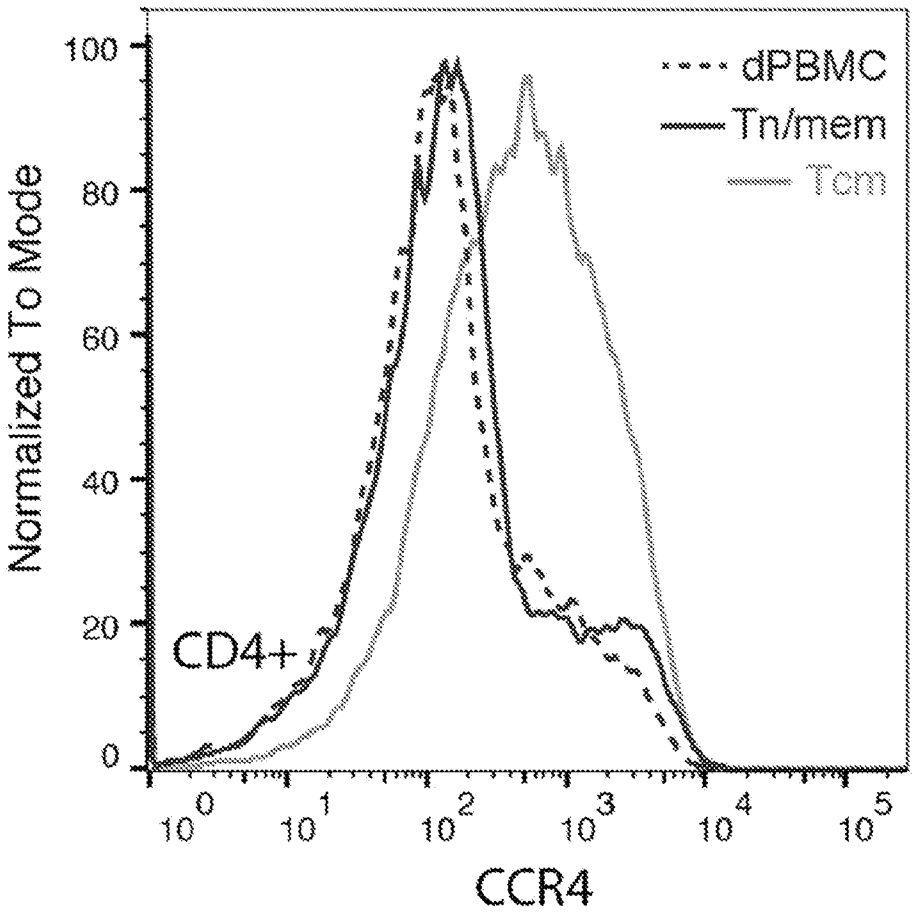

CCR4 CAR lentivirus was used to transduce human healthy donor-derived peripheral blood mononuclear cells depleted of CD14+ and CD25+ cells (dPBMC), as previously described (Priceman S J, Gerdts E A, Tilakawardane D, Kennewick K T, Murad J P, Park A K, Jeang B, Yamaguchi Y, Yang X, Urak R, Weng L, Chang W C, Wright S, Pal S, Reiter R E, Wu A M, Brown C E, Forman S J. Co-stimulatory signaling determines tumor antigen sensitivity and persistence of CAR T cells targeting PSCA+ metastatic prostate cancer. Oncoimmunology. 2018; 7(2): e1380764) as well as other cells types such as enriched T-cells (EasySep Human T cell isolation Kit. StemCell Technologies). Using EGFRt as a tracking marker, flow cytometry was used to show CAR expression as described above. All three CCR4 CAR constructs were stably expressed in T cells (FIG. 4). Seven days after dPBMC cells were transduced, cells were stained with anti-CD3 to mark T cells and anti-EGFR to mark successful incorporation of the CCR4 CAR construct. CCR4 L CAR, CCR4 EQ CAR, and CCR4 ΔCH2 CAR were all stably expressed at 7 days post-transduction (FIG. 4) and expression of EGFR was shown to be stable up to 28 days after the start of transduction (data not shown).

Example 2: CCR4 Expression in T Cell Populations

The studies described below examined CCR4 CAR T cell expansion and activity in different T cell subpopulations, such as PBMC (CD14−, CD25−), and pan-T cells.

The starting T cell population used to generate CAR T cells may influence the potency with which the CAR T cells can eliminate its target cells. There may also be differences in the proliferation of the cells during the 14 day manufacturing process.

Figure 6A:
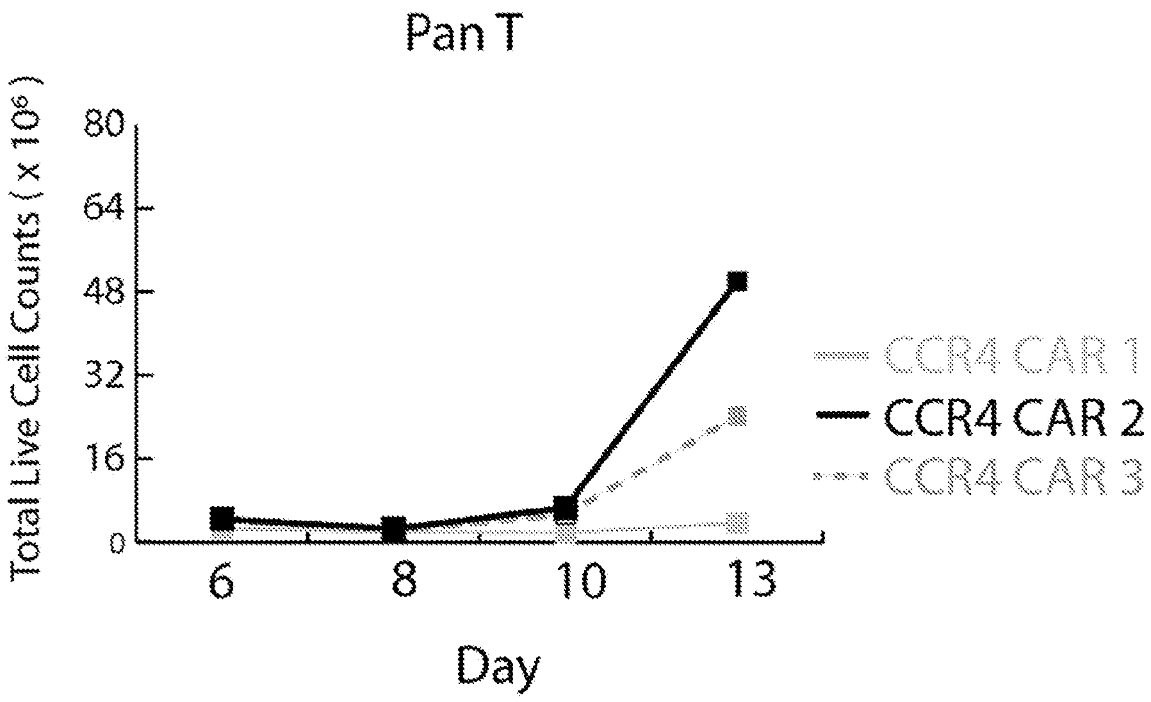
FIGS. 6A-6B shows results from a CCR4 growth curve. (A) Pan T cells from the same healthy donor with the three different CCR4 CAR constructs and tracked the live cells counts of the cells over 13 days. (C) Depleted PBMC (CD14−CD25−; also called dPBCM) cells from the same healthy donor with the three different CCR4 CAR constructs and tracked the live cells counts of the cells over 13 days.
Figure 6B:
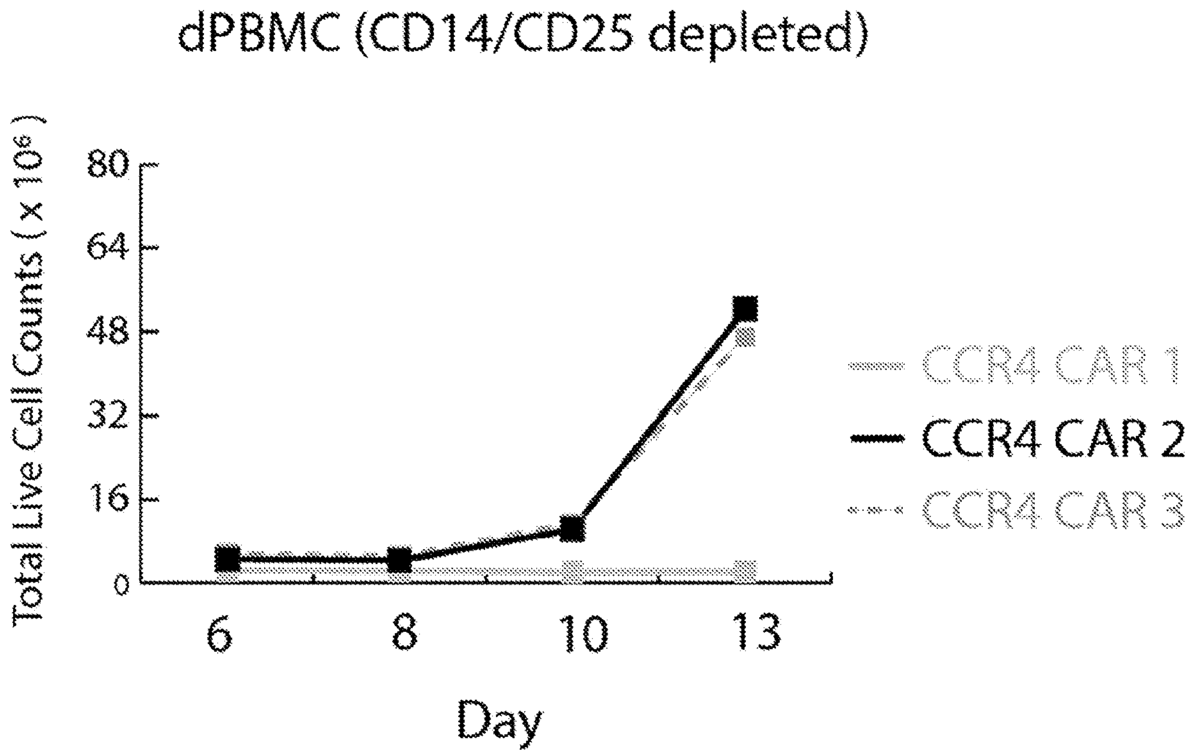

We transduced different populations of T cells from the same healthy donor with the 3 different CCR4 CAR constructs (FIG. 1) and tracked the live cells counts of the cells over 13 days. We found that CCR4 EQ CAR and CCR4 ΔCH2 CAR proliferated the best overall (FIGS. 6A-6B). We have observed that CCR4 L CAR has poorer proliferation in several independent studies with CCR4 L CAR cells generated from different healthy donors in a variety of starting T cell populations (data not shown).

Example 3: Validation that CCR4 CAR T Cells Selectively Target CCR4-Positive Cells in Vitro To determine if CCR4 CAR T cells demonstrate selective activity against CCR4-positive cancer cells, the CCR4 CAR T cells were grown in presence of either CCR4-positive or CCR4-negative cancer cells and the percentage of cancerous cells killed was quantified.

To assess antigen-dependent activity of our CCR4 CAR T cells, co-cultured assays with CCR4-positive and -negative tumor targets were conducted at an E:T ratio between 1:2 and 1:10 to determine their killing potential. The CCR4-positive T cell tumor lines used were MT-1 and CEM. The CCR4-negative cell line used was LCL, a B cell tumor cell line. We co-cultured CCR4 EQ CART cells and tumor cells at a ratio of 1 T cell for every 10 tumor cells (1:10 E:T). Using flow cytometry we then tested for the killing of tumor cells (% specific lysis) after 48 hours.

Figure 7A:
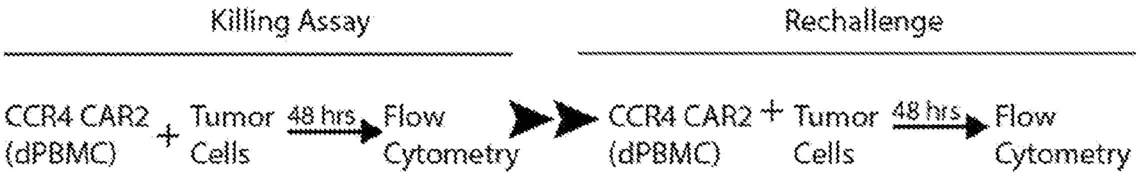
FIGS. 7A-7D shows the ability of the CCR4 CAR2 T cells to kill CCR4 expressing T cell tumor lines. (A) A schematic representation depicts a "Killing" assay followed by a "Rechallenge" assay demonstrates the ability of a CCR4 CART cell to kill CCR4 expressing T cell tumor lines. (B) Killing and rechallenge assays using CEM cells, a CCR4+ tumor cell line. (C) Killing and rechallenge assays using MT1 cells, a CCR4+ tumor cell line. (D) Killing and rechallenge assays using LCL cells, CCR4 negative B cell tumor line.
Figure 7B:
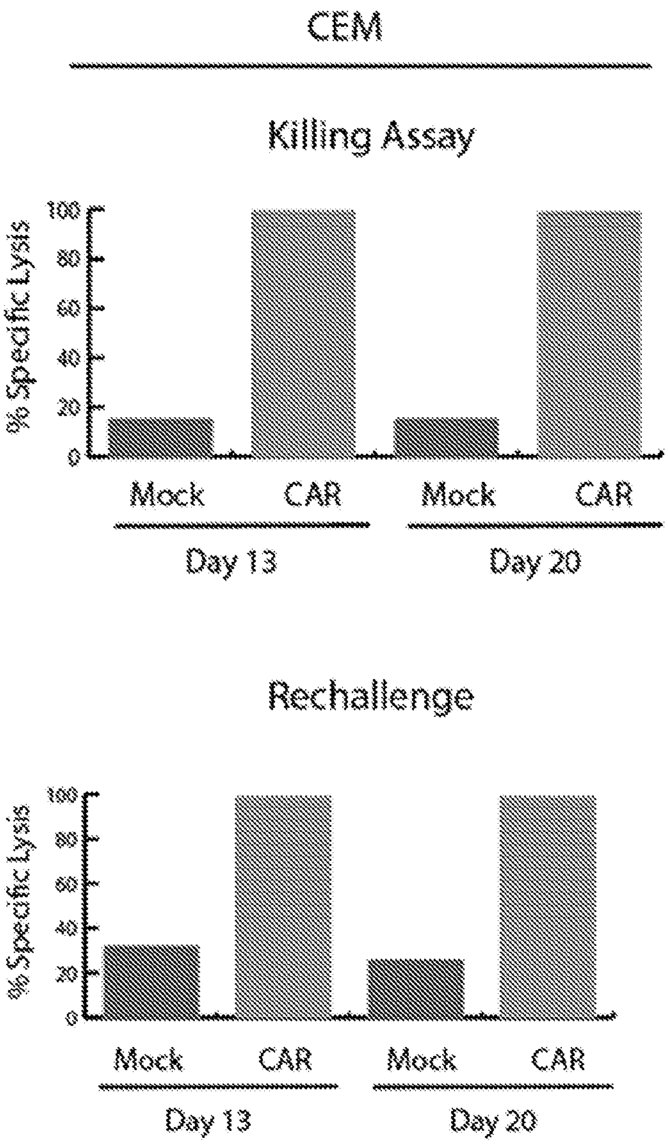
Figure 7C:
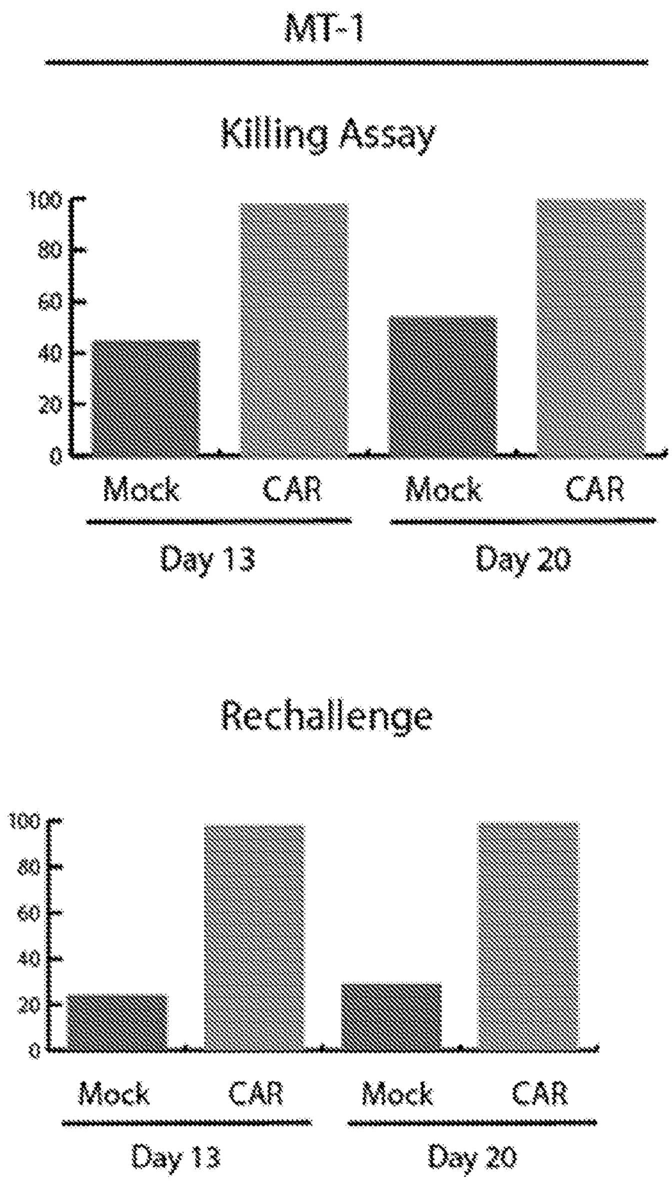
Figure 7D:
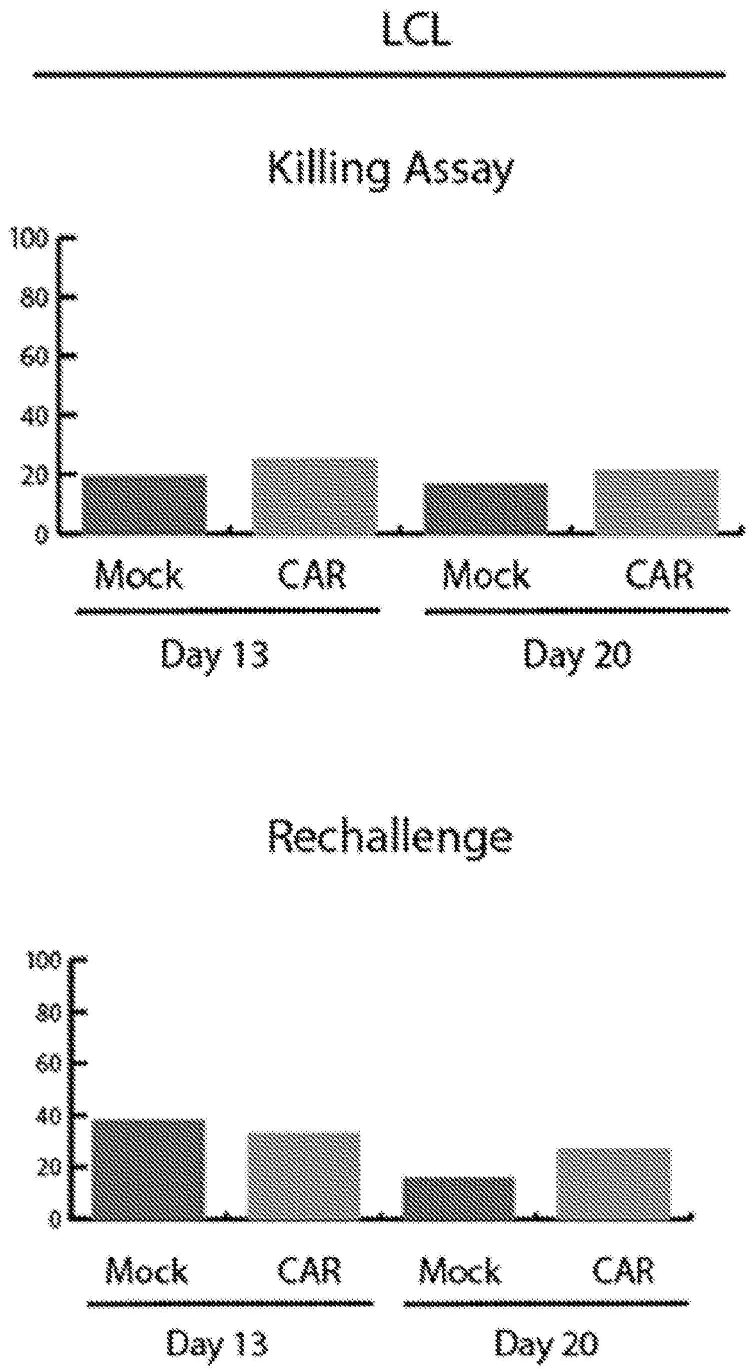

After 48 hours, antigen-specific T cell-mediated killing activity was evident with CCR4 EQ CART cells relative to Mock T cells in the CEM tumor line (FIG. 7B, top) and the MT-1 tumor cell line (FIG. 7C, top). CCR4 EQ CAR2 T cells had sustained killing at or near 100% lysis in both the CEM tumor line (FIG. 7B, top) and the MT-1 tumor cell line (FIG. 7C, top). These results at an E:T of 1:10 demonstrate the potent killing ability of CCR4 EQ CAR T cells. CCR4 EQ CAR T cells showed minimal killing of CCR4-negative LCL cells (FIG. 7D, top). CCR4 L CAR T cells and CCR4 ΔCH2 CAR T cells also killed CCR4+ tumor cells (data not shown).

Additionally, to test if CCR4 EQ CAR T cells can continue to kill tumor cells if rechallenged, we co-cultured CART cells and tumor cells at a ratio of 1:2 (1 T cell:2 tumor cells) for 48 hrs. After the 48 hours, we added additional tumor cells to the co-culture wells to an E:T of 1:2, and after an additional 48 hours, used flow cytometry to determine the % specific lysis of the tumor cells. Surprisingly, we found that the CCR4 EQ CAR T cells were able to kill CCR4+ tumor lines even when rechallenged (FIGS. 7B-7C, bottom). Both CCR4 L CAR T cells and CCR4 ΔCH2 CAR T cells also killed CCR4+ tumor cells when rechallenged (data not shown).

Example 4: Establishment of In Vivo Malignant T Cell Mouse Models

To evaluate the therapeutic potential of the CCCR4 CART cells in vivo, three mouse models were established using a variety of injection routes.

Figure 8A:
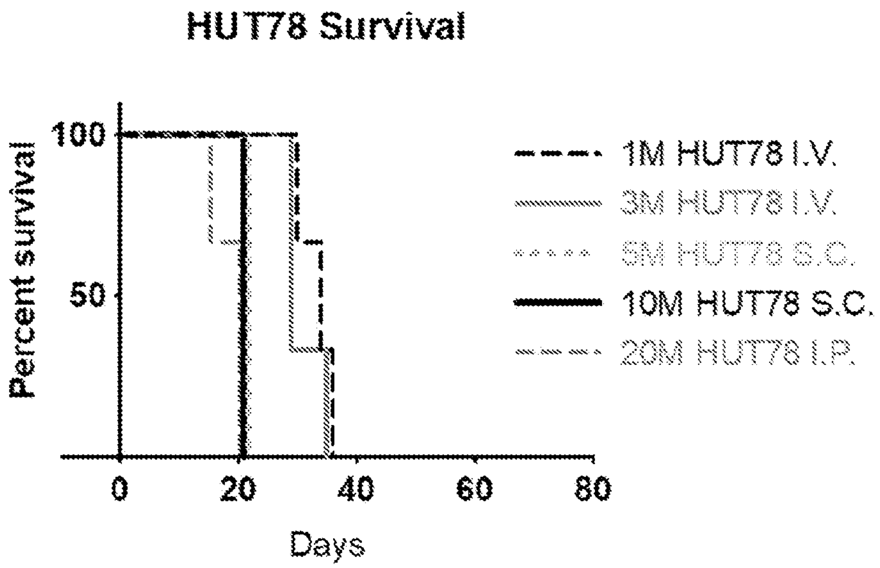
FIGS. 8A-8C shows survival curves in three mouse models engrafted with CCR4-expressing malignant T cell lines using a variety of injection routes (IP, intraperitoneal; SC subcutaneous; IV, intravenous).
Figure 8B:
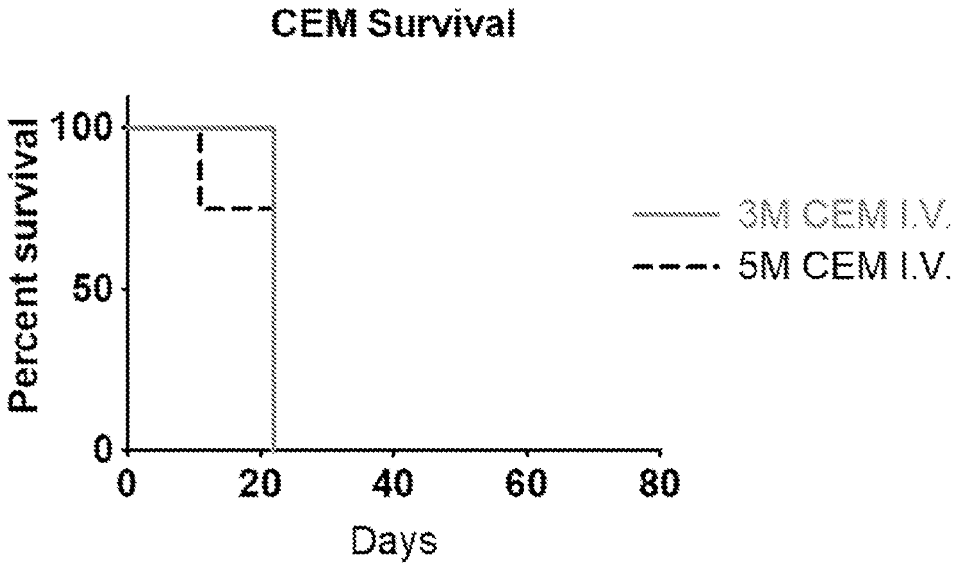
Figure 8C:
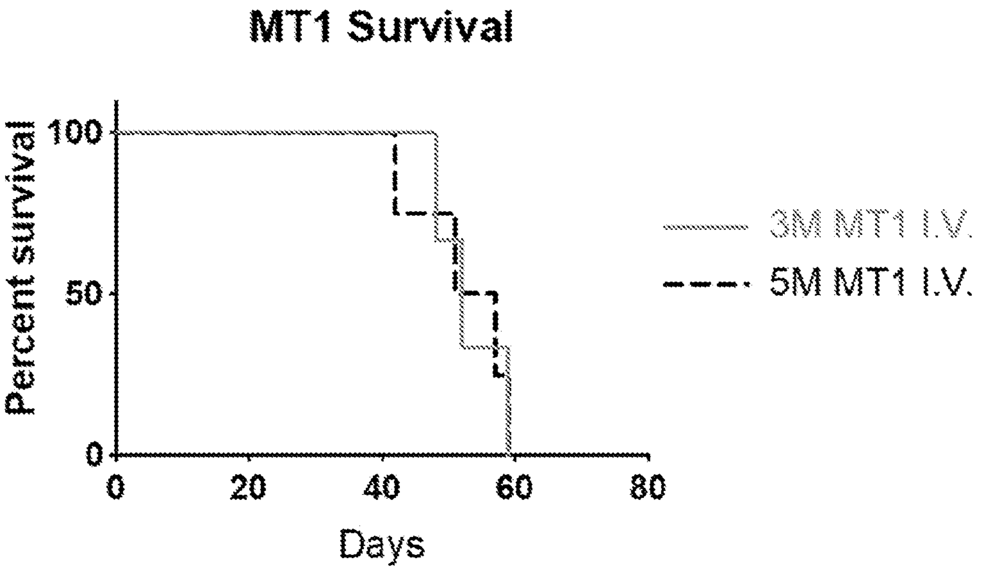

Humane endpoints were used in determining survival curves of NSG mice engrafted with CCR4 expressing malignant T cell lines. Mice were euthanized upon signs of distress such as a distended belly due to ascites, labored or difficulty breathing, apparent weight loss, impaired mobility, or evidence of being moribund. Mice were engrafted cells delivered systemically or locally with HUT78, CEM, and MT-1 via i.p., s.c., and i.v. injection (FIG. 8).

Example 5: Validation that CCR4 CAR T Cells Delivered In Vivo in a Mouse Model Exhibit Potent Anti-Tumor Activity and Confer Extended Lifespan to the Mice To evaluate in vivo efficacy of CCR4 CAR T cells to selectively target CCR4-positive cells in the CEM model, CCR4 CAR T cells were delivered and tumor size and survival was evaluated over time.

Figure 9A:
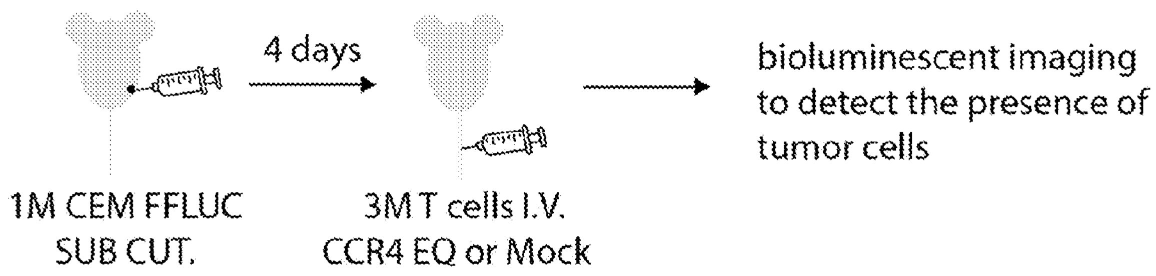
FIG. 9A-9B shows in vivo efficacy of the CCR4 CAR T cells. (A) A schematic depicts sc engraftment of CEM in NSG mice. After 4 days, mice were treated IV with the CAR T cells or mock transduced T cells and compared to a tumor only group. (B) Survival of mice treated IV with the CAR or mock transduced T cells compared to a tumor only group was monitored.
Figure 9B:
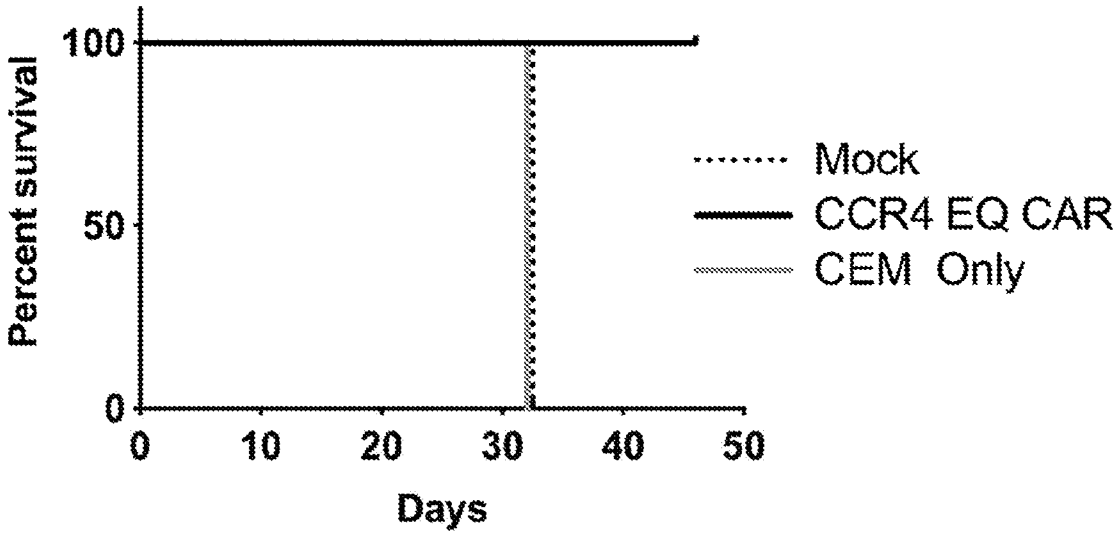
Figure 11:
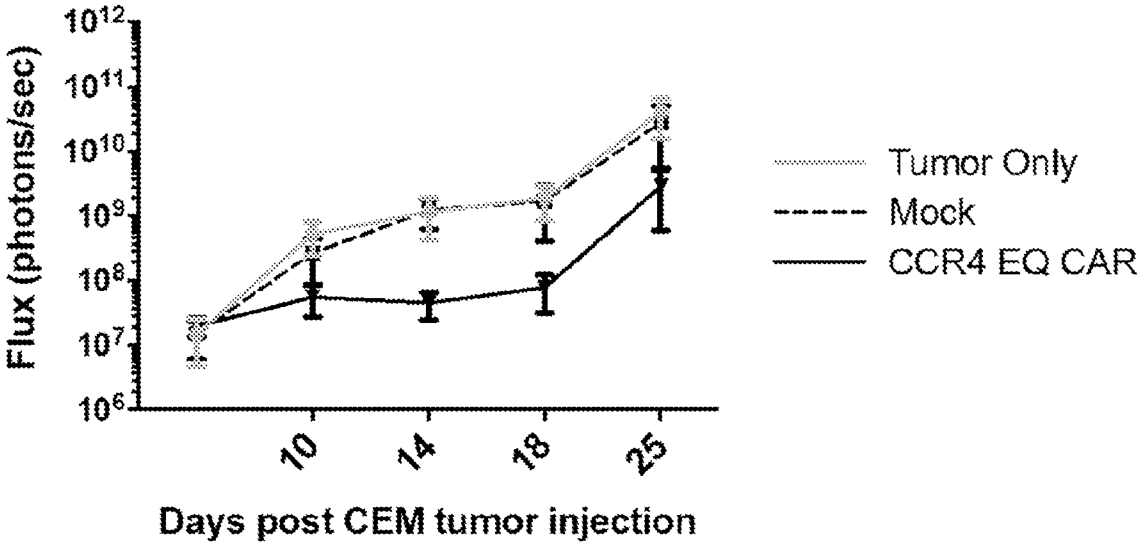
FIG. 11 shows bioluminescent detection of tumor growth following engraftment of CEM in NSG mice treated IV with the CAR T cells or mock transduced T cells and compared to a tumor only group.

CEM cells were lentivirally transduced to express firefly luciferase (ffluc) to allow for tracking of tumor growth via non-invasive optical imaging. At 4 days post tumor s.c. injection, mice were treated with Mock or CCR4 EQ CAR2 T cells ($3.0\times10^6$) by systemic intravenous (i.v.) delivery (FIG. 9A). Rapid anti-tumor effects were observed in mice treated with CCR4 EQ CAR T cells via i.v. delivery, reaching a maximal anti-tumor response 1-2 weeks following treatment. Anti-tumor responses in mice were durable for 3-4 weeks, but ultimately tumor recurrences were observed in mice. Delivery of CCR4 EQ CAR T cells significantly extended survival of mice (FIG. 9B and FIG. 11).

Example 6: Validation that CCR4 CAR T Cells Delivered In Vivo in a Mouse Model Exhibit Potent Anti-Tumor Activity and Confer Extended Lifespan to the Mice To evaluate in vivo efficacy of CCR4 CAR T cells in a disseminated model, CCR4 CAR T cells were delivered to the HUT78 mouse model, and tumor size and survival was evaluated over time.

HUT78 were cultured in IMDM (Iscove's Modified Dulbecco's Medium; Fisher Scientific) with 20% FBS. For the HUT78 in vivo model, CD4 and CD8 enriched cells from PBMC via incubation of PBMC with anti-CD4 and anti-CD8 microbeads (Miltenyi Biotech). Another T cell population used were T cells generated by negative selection of PBMC. Human T cell isolation kit from StemCell was also used.

Figure 12A:
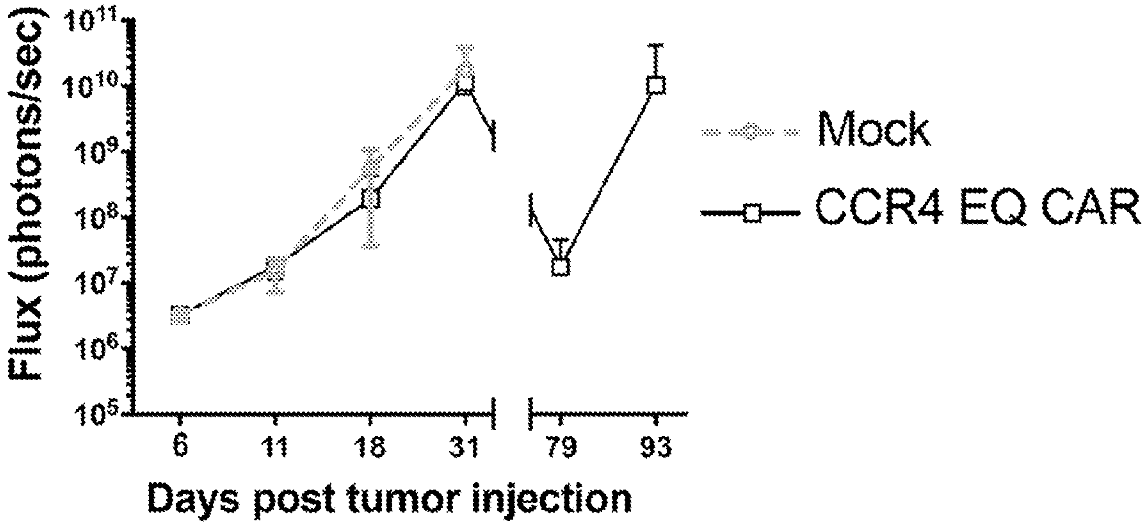
FIGS. 12A-12B show in vivo efficacy of the CCR4 CAR T cells in a HUT78 mouse model. (A) Bioluminescent detection of tumor growth following IV engraftment of HUT78 in NSG mice. After 10 days, mice were treated IV with the CART cells or mock transduced T cells. (B) Survival of mice treated IV with the CAR or mock transduced T cells was monitored.
Figure 12B:
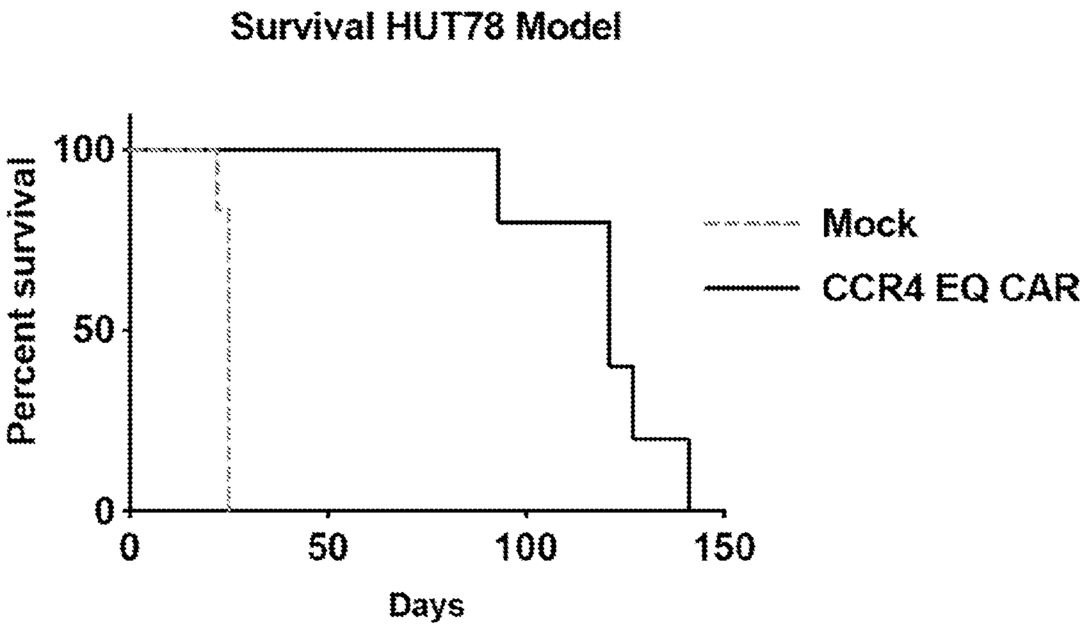

For in vivo tumor studies, HUT78 cells ($1.0\times10^6$) were prepared in a final volume of 150 μl HBSS−/− and engrafted in 6 to 8 week old female or male NSG mice by injection. HUT78 Animal model is a disseminated model. In some embodiments, engraftment comprises subcutaneous (s.c.) injection or intravenous (i.v.) injection. HUT78 cells were lentivirally transduced to express firefly luciferase (ffluc) to allow for tracking of tumor growth via non-invasive optical imaging. At 10 days post tumor i.v. injection, mice were treated with Mock or CCR4 EQ CAR2 T cells ($3.0\times10^6$) by systemic intravenous (i.v.) (FIG. 12A). Anti-tumor effects were observed in mice treated with CCR4 EQ CAR T cells following treatment. Delivery of CCR4 EQ CART cells significantly extended survival of mice (FIG. 12B).

Example 7: Inducible CCR4 CAR T Cells

In some circumstances it is desirable to control expression of a CCR4 CAR. For example, after a vector is introduced into population of T cells, the cells are expanded to prepare a sufficient number of cells to use therapeutically. During this expansion stage, it can be desirable to reduce or nearly eliminate expression of the CCR4 CAR, for example, to reduce any fratricide. A system that uses Tet-Off control can be useful (Das et al. 2016 *Current Gene Therapy* 16:156). Thus, an expression vector for expression of a CCR4 CAR can express the CCR4 CAR under the control of an inducible promoter that includes several copies of the tet operator and minimal promoter. The vector can also encode a fusion protein comprising the transcription activation of domain of VP16 fused to TetR. In the presence of tetracycline or doxycycline, expression of the CCR4 CAR is repressed. When tetracycline or doxycycline is not present, the CCR4 is expressed. Thus, T cells harboring a nucleic acid encoding CCR4 CAR can be expanded under conditions in which CCR4 CAR expression is repressed. When a desired number of cells is obtained, tetracycline or doxycycline is withdrawn to induce expression.

Figure 13B:
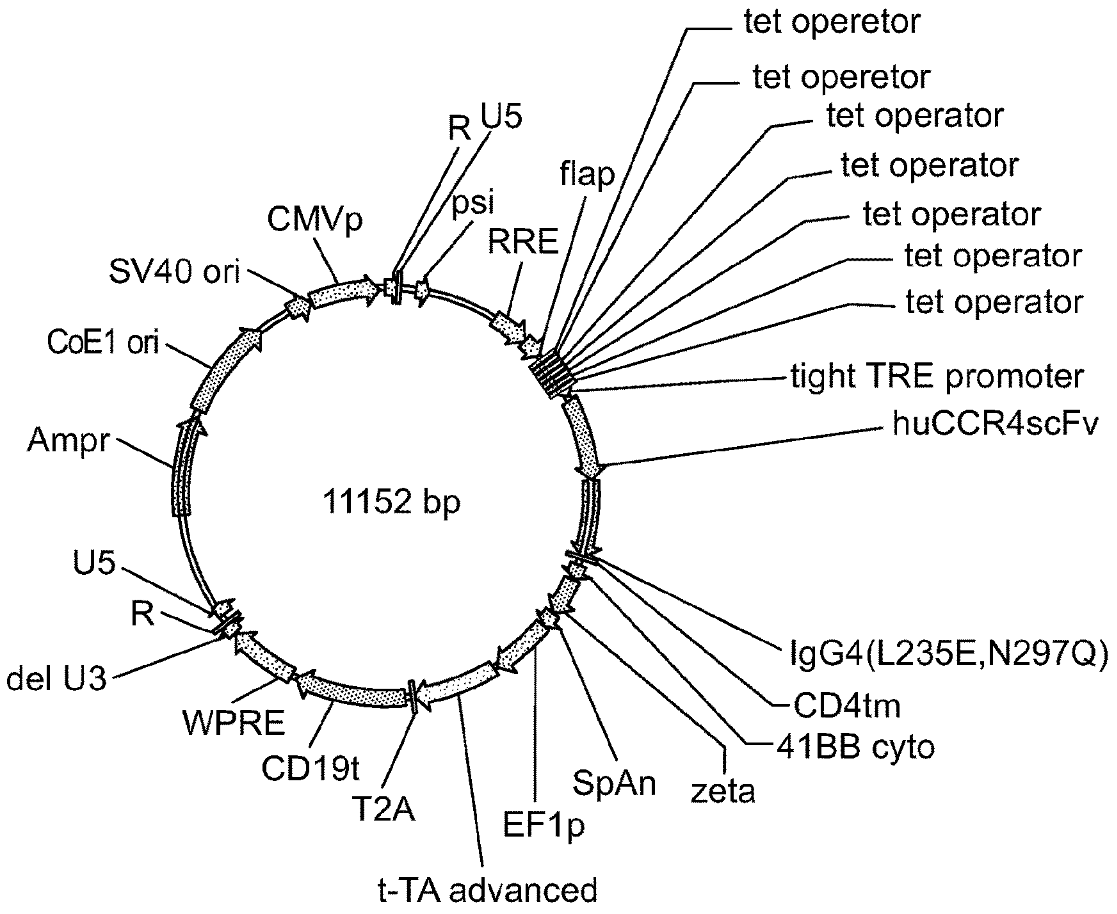
Figure 13C:
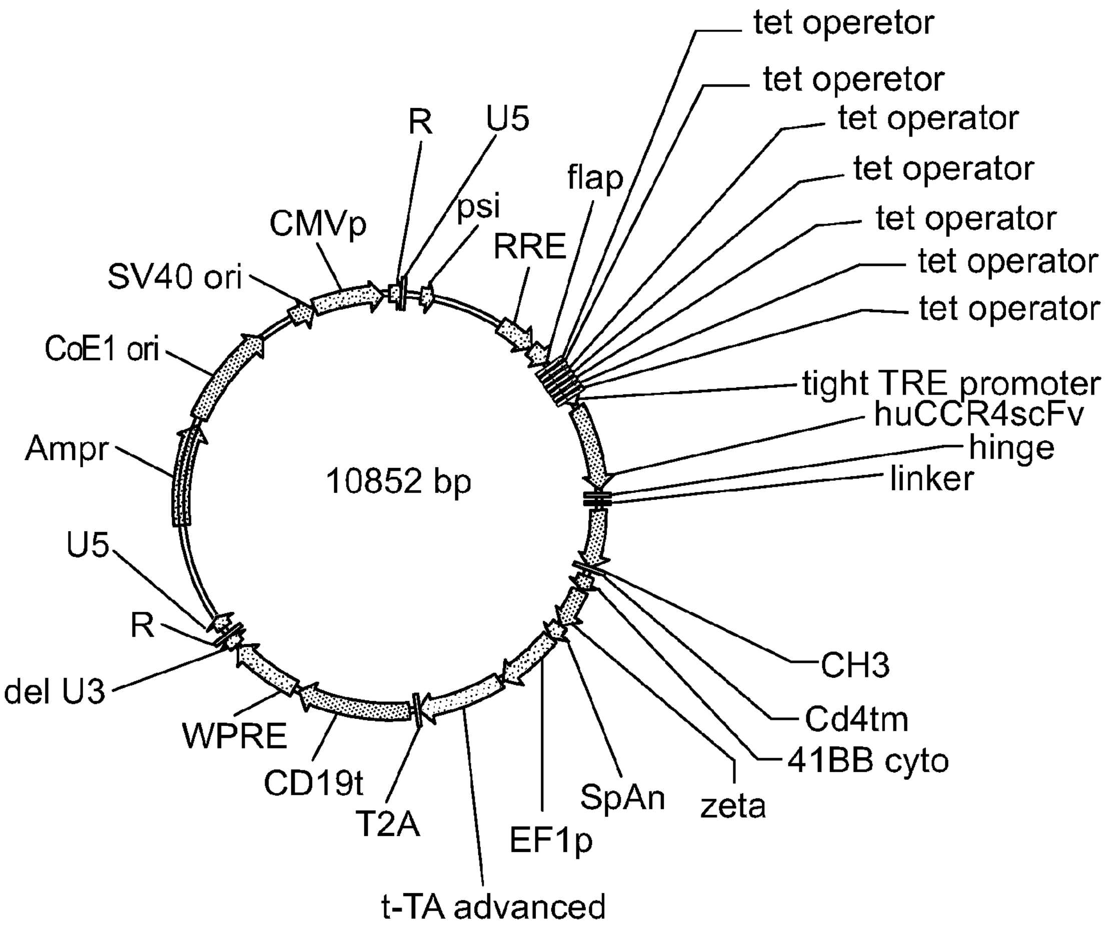
Figure 13D:
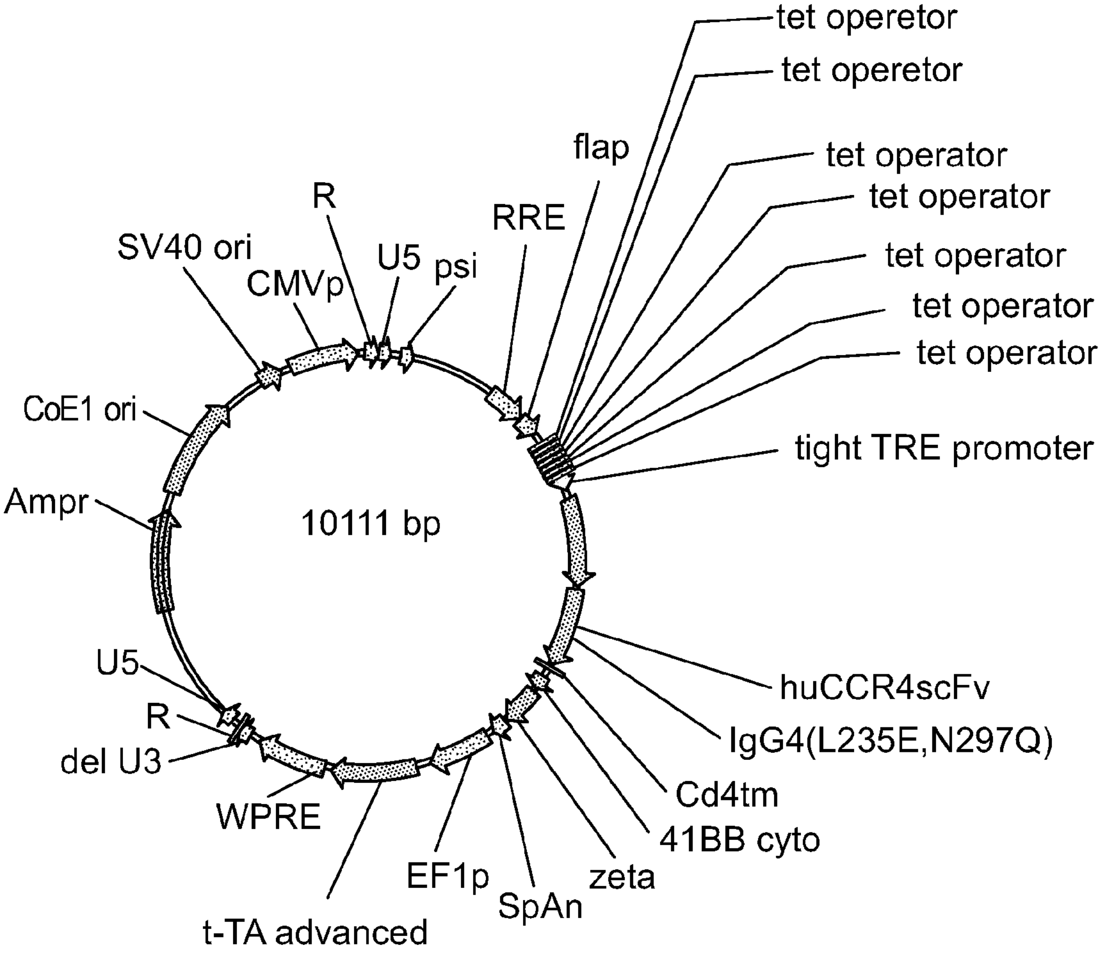
Figure 13E:
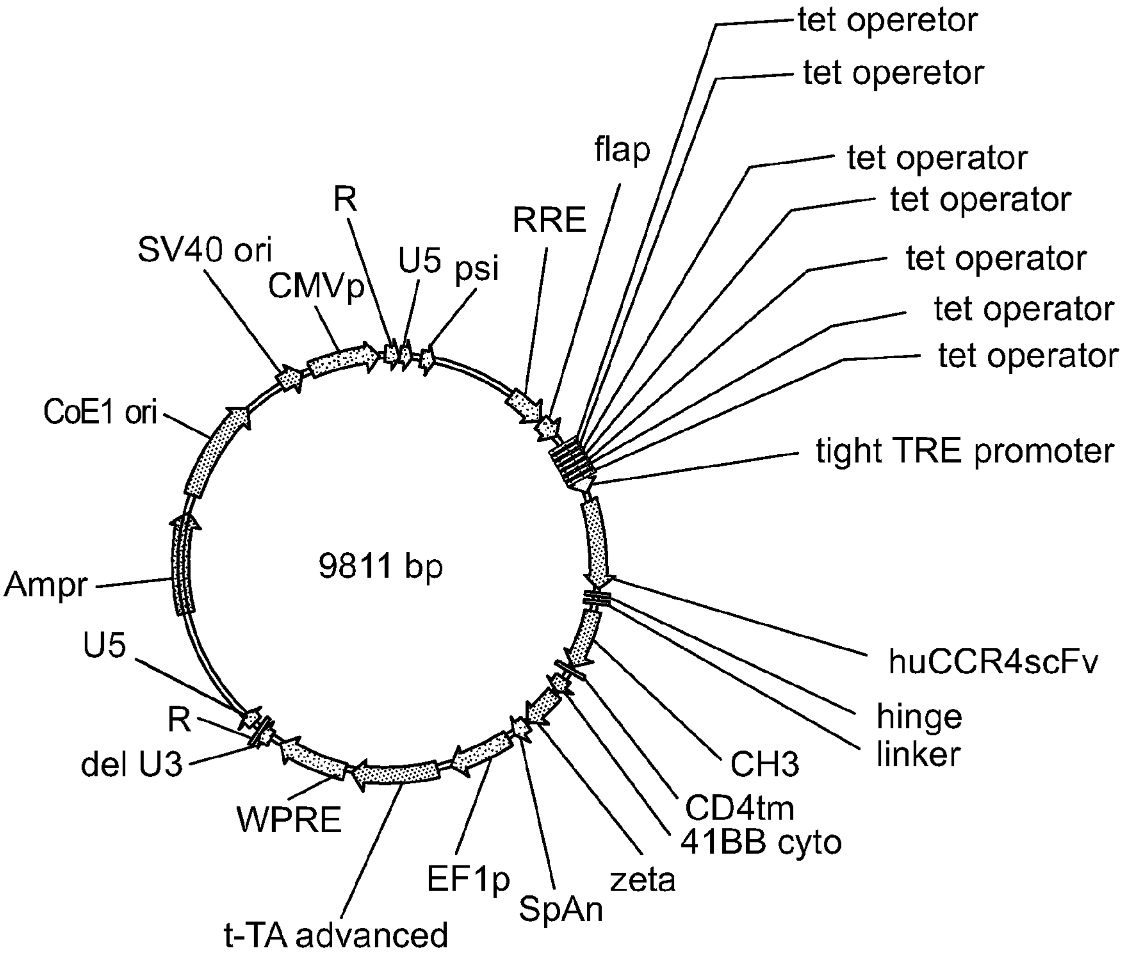

FIG. 13A depicts schematic diagrams of four inducible CCR4 CAR constructs. FIG. 13B shows the plasmid map of inducible CAR1 (CCR4 EQ with CD19t). FIG. 13C shows the plasmid map of inducible CAR2 (CCR4 CH3 with CD19t). FIG. 13D shows the plasmid map of inducible CAR3 (CCR4 EQ). FIG. 13E shows the plasmid map of inducible CAR4 (CCR4 CH3).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All references are herein incorporated in their entirety for any and all purposes.

What is claimed is:

1. A chimeric antigen receptor (CAR) or a polypeptide comprising the amino acid sequence of SEQ ID NO: 29, 30, 31, 38, 39, or 40.

2. A population of human T cells comprising the CAR or polypeptide of claim 1.

3. The CAR or polypeptide of claim 1, wherein the CAR or the polypeptide consists of the amino acid sequence of SEQ ID NO: 29, 30, 31, 38, 39, or 40.

4. The population of human T cells of claim 2, wherein the population of human T cells comprise central memory T cells, naive memory T cells, CD4+ cells and CD8+ cells enriched from PBMC cells, T cells isolated via negative depletion, or PBMC substantially depleted for CD25+ cells and CD14+ cells.

5. A method of treating T cell lymphoma in a patient comprising administering a population of autologous or allogeneic human T cells expressing the CAR or polypeptide of claim 1, wherein the T cell lymphoma comprises cells expressing CCR4.

6. The method of claim 5, wherein the population of human T cells expressing the chimeric antigen receptor or the polypeptide is administered by single or repeat dosing.

7. The CAR or polypeptide of claim 1, wherein the CAR or the polypeptide comprises the amino acid sequence of SEQ ID NO: 29.

8. The CAR or polypeptide of claim 1, wherein the CAR or the polypeptide comprises the amino acid sequence of SEQ ID NO: 30.

9. The CAR or polypeptide of claim 1, wherein the CAR or the polypeptide comprises the amino acid sequence of SEQ ID NO: 31.

10. The CAR or polypeptide of claim 1, wherein the CAR or the polypeptide comprises the amino acid sequence of SEQ ID NO: 38.

11. The CAR or polypeptide of claim 1, wherein the CAR or the polypeptide comprises the amino acid sequence of SEQ ID NO: 39.

12. The CAR or polypeptide of claim 1, wherein the CAR or the polypeptide comprises the amino acid sequence of SEQ ID NO: 40.

* * * * *